United States Patent
Chalvignac et al.

(10) Patent No.: US 9,616,192 B2
(45) Date of Patent: Apr. 11, 2017

(54) BREATHABLE GAS INLET CONTROL DEVICE FOR RESPIRATORY TREATMENT APPARATUS

(75) Inventors: Philippe Auguste Chalvignac, Moissy-Cramayel (FR); Arthur Kin-Wai Yee, Bella Vista (AU); David Creusot, Bella Vista (AU); Enrico Brambilla, Milan (IT)

(73) Assignee: ResMed Paris SAS (FR)

( * ) Notice: Subject to any disclaimer, the term of this patent is extended or adjusted under 35 U.S.C. 154(b) by 1117 days.

(21) Appl. No.: 13/635,935

(22) PCT Filed: Mar. 25, 2011

(86) PCT No.: PCT/AU2011/000341
§ 371 (c)(1),
(2), (4) Date: Sep. 19, 2012

(87) PCT Pub. No.: WO2011/116428
PCT Pub. Date: Sep. 29, 2011

(65) Prior Publication Data
US 2013/0008444 A1 Jan. 10, 2013

Related U.S. Application Data

(60) Provisional application No. 61/317,483, filed on Mar. 25, 2010.

(51) Int. Cl.
*A61M 16/20* (2006.01)
*A61M 16/00* (2006.01)
(Continued)

(52) U.S. Cl.
CPC ...... *A61M 16/203* (2014.02); *A61M 16/0051* (2013.01); *A61M 16/0066* (2013.01);
(Continued)

(58) Field of Classification Search
CPC .............. A61M 16/00; A61M 16/0051; A61M 16/0057; A61M 16/0066; A61M 16/0069; A61M 16/20; A61M 16/201–16/207
(Continued)

(56) References Cited

U.S. PATENT DOCUMENTS

| 4,637,385 A * | 1/1987 | Rusz ..................... A61M 16/00 128/204.21 |
| 5,694,926 A * | 12/1997 | DeVries ................ A61M 16/00 128/204.21 |

(Continued)

FOREIGN PATENT DOCUMENTS

| JP | 11-514259 A | 12/1999 |
| JP | 2002-119595 | 4/2002 |

(Continued)

OTHER PUBLICATIONS

Extended European Search Report for Application No. EP11758688 dated Mar. 11, 2016.
International Search Report for Application No. PCT/US2011/000341 dated Jul. 26, 2011.

*Primary Examiner* — Steven Douglas
*Assistant Examiner* — Colin W Stuart
(74) *Attorney, Agent, or Firm* — Lerner, David, Littenberg, Krumholz & Mentlik, LLP

(57) ABSTRACT

A breathable gas inlet control device permits flow regulation at the inlet of a flow generator for a respiratory treatment apparatus such as a ventilator or continuous positive airway pressure device. The device may implement a variable inlet aperture size based on flow conditions. In one embodiment, an inlet flow seal opens or closes the inlet to a blower in accordance with changes in pressure within a seal activation chamber near the seal. The seal may be formed by a flexible membrane. A controller selectively changes the pressure of the seal activation chamber by controlling a set of one or more flow control valves to selectively stop forward flow, prevent back flow or lock open the seal to permit either back flow or forward flow. The controller may set the flow control valves as a function of detected respiratory conditions based on data from pressure and/or flow sensors.

37 Claims, 19 Drawing Sheets

(51) Int. Cl.
*A61M 16/12* (2006.01)
*A61M 16/10* (2006.01)
*A61M 16/16* (2006.01)

(52) U.S. Cl.
CPC .... *A61M 16/0069* (2014.02); *A61M 16/1095* (2014.02); *A61M 16/12* (2013.01); *A61M 16/20* (2013.01); *A61M 16/201* (2014.02); *A61M 16/204* (2014.02); *A61M 16/205* (2014.02); *A61M 16/206* (2014.02); *A61M 16/207* (2014.02); *A61M 16/16* (2013.01); *A61M 16/202* (2014.02); *A61M 2016/0027* (2013.01); *A61M 2202/0208* (2013.01); *A61M 2205/3365* (2013.01); *A61M 2205/502* (2013.01); *A61M 2205/52* (2013.01)

(58) Field of Classification Search
USPC ............ 128/205.24, 204.18, 204.21, 204.27, 128/204.26; 251/5, 14, 28, 33, 43, 50
See application file for complete search history.

(56) References Cited

U.S. PATENT DOCUMENTS

| | | | |
|---|---|---|---|
| 5,906,203 | A | 5/1999 | Klockseth et al. |
| 6,182,657 | B1* | 2/2001 | Brydon ............. A61M 16/0057 128/204.18 |
| 6,722,359 | B2 | 4/2004 | Chalvignac |
| 2003/0062045 | A1* | 4/2003 | Woodring ......... A61M 16/0051 128/204.18 |

FOREIGN PATENT DOCUMENTS

| | | | |
|---|---|---|---|
| JP | 2006521152 | A | 9/2006 |
| JP | 2008546476 | A | 12/2008 |
| WO | 9218201 | A1 | 10/1992 |
| WO | 9604043 | A1 | 2/1996 |
| WO | 9710868 | A1 | 3/1997 |
| WO | 9741812 | A1 | 11/1997 |
| WO | 2005097248 | A1 | 10/2005 |

* cited by examiner

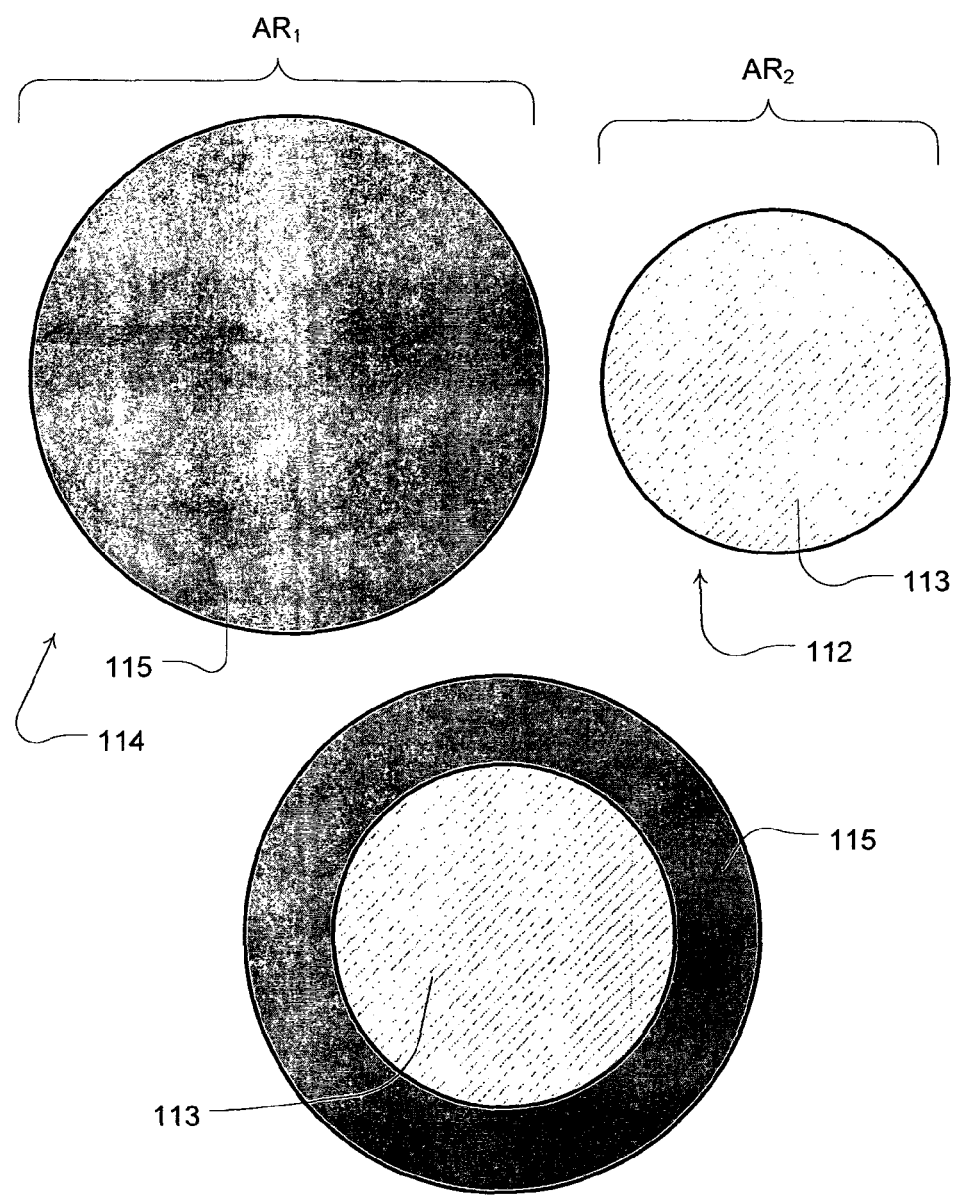
FIG. 1-A

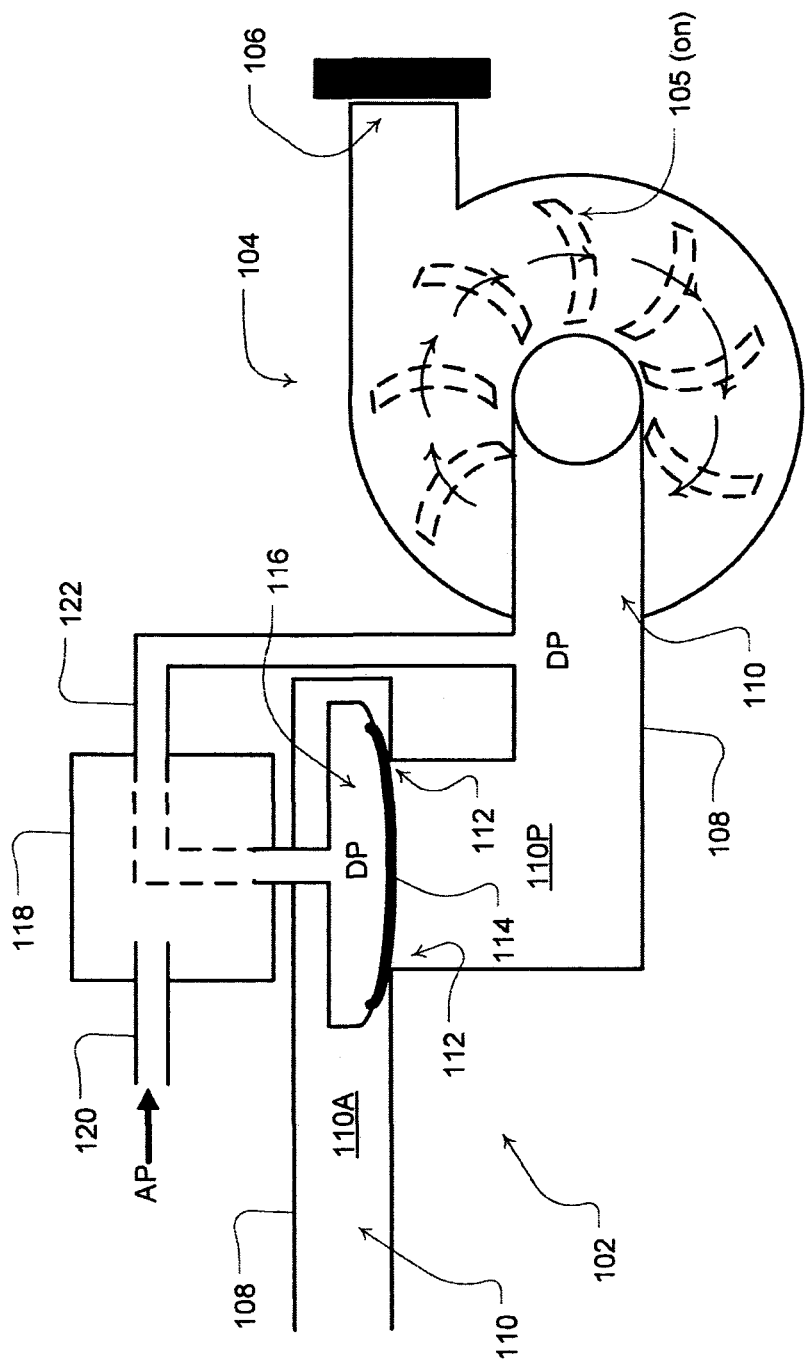
FIG. 3-A

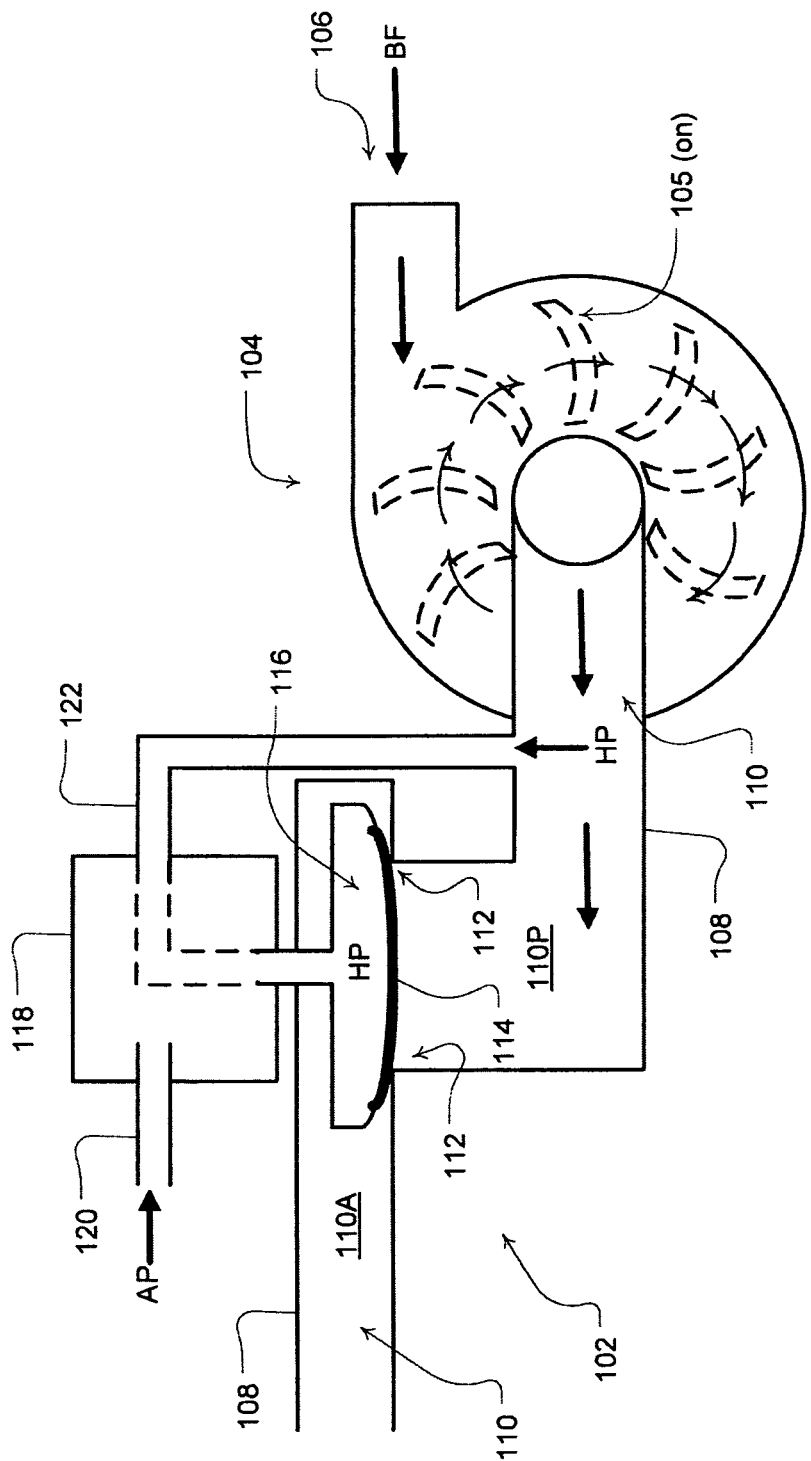
FIG. 3-B

BREATHABLE GAS INLET CONTROL DEVICE FOR RESPIRATORY TREATMENT APPARATUS

CROSS REFERENCE TO RELATED APPLICATIONS

The present application is a national phase entry under 35 U.S.C. §371 of International Application No. PCT/AU2011/000341 filed on Mar. 25, 2011, published in English, which claims priority from U.S. Provisional Patent Application No. 61/317,483, filed Mar. 25, 2010, all of which are incorporated herein by reference.

FIELD OF THE TECHNOLOGY

The present technology relates to valves for controlling gas flow in respiratory treatment apparatus. More specifically, it relates to valves to limit gas flow, such as inlet gas flow, to a flow generator in respiratory treatment apparatus such as continuous positive airway pressure treatment devices, ventilator devices or other airflow devices for treating respiratory-related conditions.

BACKGROUND OF THE TECHNOLOGY

Respiratory treatment apparatus can function to supply a patient with a supply of clean breathable, gas (usually air, with or without supplemental oxygen) at a therapeutic pressure or pressures, at appropriate times during the subject's breathing cycle. Pressure changes may be implemented in a synchronized fashion so as to permit greater pressures during inspiration and lower pressures during expiration. Therapeutic pressure is also known as the ventilation pressure.

Respiratory treatment apparatus typically include a flow generator, an air filter, a mask, an air delivery conduit connecting the flow generator to the mask, various sensors and a microprocessor-based controller. Optionally, in lieu of a mask, a tracheotomy tube, may also serve as a patient interface. The flow generator may include a servo-controlled motor, volute and an impeller that forms a blower. In some, cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as ah alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

These devices may be used for the treatment of many conditions, for example respiratory insufficiency or failure due to lung, neuromuscular or musculoskeletal disease and diseases of respiratory control. They may also be used for conditions related to sleep disordered breathing (SDB) (including mild obstructive sleep apnea (OSA)), allergy induced upper airway obstruction or early viral infection of the upper airway.

It may be desirable to develop further methods and devices for controlling the flow of breathable gas in a respiratory treatment apparatus during operations.

SUMMARY OF THE TECHNOLOGY

An aspect of some embodiments of the current technology is to provide a flow control device for a respiratory treatment apparatus.

Another aspect, of some embodiments of the technology is to provide a variable inlet for a respiratory treatment apparatus.

A still further aspect of some embodiments of the technology is to provide an inlet flow control device that is adjustable in accordance with patient flow.

A yet further feature of some embodiments of the technology is to provide a flow control device to prevent back flow.

A still further aspect of some embodiments, of the technology is to provide such a flow control device to prevent a back flow or return of breathable gas in a respiratory treatment apparatus based on detected conditions.

Another aspect of some embodiments of the technology is to provide a flow control seal for an inlet of a flow generator.

For example, in some embodiments of the technology, a respiratory treatment apparatus may be configured to provide a flow of breathable gas to a patient. The apparatus may include a gas inlet having a variable aperture that is adjustable between closed and fully open and a gas outlet. A flow generator of the apparatus may be adapted to provide a supply of pressurized breathable gas from the gas inlet, and to the gas outlet. The apparatus may also include a controller to control, the level of pressure generated by the flow generator. The aperture may vary in opening size as a function of a level of flow of breathable gas provided adjacent to the gas outlet. The variable aperture may include a flexible seal. It may also be configured for proportional opening over a range of flow values where the range of flow is between a first flow value and a second flow value. In some embodiments, the first flow value may be approximately 0 liters per minute and the second flow value may be approximately 70 liters per minute. Optionally, the variable aperture may be configured at a fixed opening size for flow values above the range of flow. The variable aperture may also be configured to be closed at the first flow value of the range of flow. The variable aperture may also include a seal activation chamber. The pressure of the seal activation chamber may be set by control of one or more electromechanical valves. The controller may set the electromechanical valve as a function of a measure of the level of flow of breathable gas. Optionally, the aperture may include an electro-mechanical valve and the controller may be configured to set a size of an opening of the electromechanical valve as a function of a measure of the level of flow of breathable gas.

In some embodiments of the technology, a respiratory treatment apparatus is configured to provide a supply of pressurized breathable gas to a patient in successive respiratory cycles where each cycle includes an inspiration phase and an expiration phase. The apparatus may include a gas inlet, a gas outlet and a flow generator that is adapted to receive an inlet flow of breathable gas from the gas inlet and to pressurize the breathable, gas prior to delivery to the gas outlet. A controller of the apparatus may then be adapted to control the level of pressure generated by the flow generator to provide an inspiratory pressure and an expiratory pressure wherein during at least a portion of the expiration phase the inlet flow to the flow generator is interrupted to facilitate the reduction, in pressure from the inspiratory pressure to the expiratory pressure. This interruption of the inlet flow may then unload a blower of the flow generator. In some such embodiments, the controller may be configured to interrupt the inlet flow by setting one or more electro-mechanical valves. For example, the apparatus may include a flexible seal in a flow path of the inlet and a seal activation chamber proximate to the flexible seal. The setting of the electro-mechanical valve may then control a pressure level of the seal activation chamber.

In some embodiments of the present technology, a flow generator for a respiratory treatment apparatus includes a motor, a volute and an impeller coupled with the motor. A housing for the impeller has a gas inlet and a gas outlet. The gas outlet is adaptable for a conduit of a patient interface to deliver breathable gas as a respiratory treatment. The apparatus also includes an inlet flow seal positioned to selectively open and close the gas inlet. The inlet flow seal has a first side internally proximate to an inlet chamber of the gas inlet and the inlet flow seal has a second side, externally proximate to the inlet chamber of the gas inlet. The seal activation chamber is configured proximate to the second side of the inlet flow seal to permit a negative pressure in the seal activation chamber to open the gas inlet to a flow of breathable gas.

In some embodiments, the housing also includes first and second ports and a pressure communication conduit to connect a posterior portion of the inlet chamber and the seal activation chamber for pressure communication such that a negative pressure in the inlet chamber results in a negative pressure in the seal activation chamber. Optionally, the flow generator may also include a first flow control valve coupled with the pressure communication conduit. The first flow control valve may be configured to selectively switch the seal activation chamber to the pressure in the pressure communication conduit associated with the inlet chamber pressure or to atmospheric pressure.

In some embodiments, the negative pressure in the seal activation chamber is due to the flow of breathable gas flowing towards the gas outlet. Moreover, this flow can be controlled by a breathing cycle. Thus, configuration of the seal activation chamber and the setting of the flow control valve may allow flow to a patient from the inlet through the flow generator and to the outlet.

Optionally, the negative pressure in the seal activation chamber may be discontinued when the flow control valve is set to open to atmospheric pressure resulting in a substantial ambient pressure equalization in the seal activation chamber. This equalization may then permit closure of the gas inlet to a flow of breathable gas such as the flow from the inlet through the flow generator and to the outlet.

Back flow through the gas inlet may also be prevented when the device is set to permit equalization between the seal activation chamber and the gas inlet chamber. The back flow from the gas outlet to the gas inlet increases pressure in the inlet chamber and the seal activation chamber such that the increase in pressure permits closure of the gas inlet with the seal.

In still further embodiment a second flow control valve is coupled with the first flow control valve. The second flow control valve may be configured to selectively switch the gas inlet of the first flow control valve to pressure of the gas outlet or ambient pressure. The switch to ambient pressure may be provided directly to ambient or to the anterior portion of the inlet chamber which can be substantially equivalent to ambient pressure.

In some embodiments, the flow control, device may be selectively set to permit back flow. For example, the apparatus may set one or more control valves to seal a desired pressure level within the seal activation chamber such that the seal activation chamber discontinues equalizing with a pressure of the gas inlet chamber and an ambient pressure. The sealed pressure level therein, which may be a negative pressure, can lock the inlet flow seal in an open position even when the pressure of the inlet chamber increases due to the back flow.

Optionally, a controller of the flow generator may be configured to set the first flow control valve to permit a negative pressure in the seal activation chamber to open the gas inlet to a flow of breathable gas in response to a detection of a condition of inspiration. The controller may also be configured to set the first and optionally the second flow control valves to discontinue the negative pressure in the seal activation chamber to close the gas inlet to a flow of breathable gas in response to a detection of a condition of expiration.

The technology may also be implemented as a respiratory treatment apparatus that includes a flow generator to produce a breathable gas at a pressure above atmospheric pressure for a pressure therapy regime. The flow generator may include a gas inlet and a gas outlet, where the gas outlet is adaptable for a conduit of a patient interface to deliver the breathable gas. The apparatus may also include a controller to control the flow generator to produce the breathable gas according to a pressure therapy regime. An inlet flow seal of the apparatus may be positioned to selectively open and close the gas inlet where the inlet flow seal has a first side internally proximate to an inlet chamber of the gas inlet and a second side externally proximate to the inlet chamber of the gas inlet. The apparatus may also include a seal activation chamber proximate to the second side of the inlet flow seal wherein a negative pressure in the seal activation chamber permits opening of the gas inlet to a flow of breathable gas.

In some embodiments of the apparatus, a pressure, communication conduit connects the interior inlet chamber and the seal activation chamber for pressure communication such that a change in pressure in the interior inlet chamber changes the pressure in the seal activation chamber. In still further embodiments of the apparatus, a first flow control valve is coupled with the seal activation chamber and is configured to selectively switch between the pressure communication conduit and atmospheric pressure under control of the controller. In some further embodiments a second flow control valve of the apparatus may be coupled with the first control valve and be configured to selectively switch between (a) equalizing pressure (permitting flow) between the gas inlet and the gas outlet and (b) equalizing pressure (permitting flow) between the gas inlet and the first control valve. In such a case, the pressure at the gas inlet may be substantially ambient pressure.

The flow generator of the apparatus may include a motor, volute and an impeller configured between the gas inlet and the gas outlet. Similar to previously described embodiments, one or more of the valves may be set to control the pressure in the chamber and the seal so as to permit flow, stop flow, prevent back flow and permit back flow.

In some embodiments of the technology, a system regulates flow to a flow generator in a respiratory treatment apparatus. The system may include a gas inlet to a flow generator through which a flow of breathable gas is drawn. The system may also include means for sealing off the flow at the gas inlet. The means for sealing may have a first side internally proximate to an inlet chamber of the gas inlet and a second side externally proximate to the inlet chamber of the gas inlet. The system may also include a chamber means that is proximate to the second side of the means for sealing wherein a negative pressure therein opens the gas inlet at the means for sealing. The system may also include a means for changing pressure to the chamber means in accordance with a change in pressure in the gas inlet. Still further, the system may include means for selectively discontinuing the change in pressure in the chamber means while permitting the change in pressure in the gas inlet.

Optionally, the aforementioned embodiments may also include an oxygen input port coupled to the inlet to inject oxygen gas into the gas inlet.

Additional features of the present respiratory treatment apparatus technology will, be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including:

FIG. 1-A is a diagram illustration an area ratio between a seal and an inlet aperture in an example embodiment of the technology;

FIG. 3-A is a schematic diagram illustrating a blocked-flow operation of the components of FIG. 1;

FIG. 3-B is a schematic diagram illustrating a patient back flow operation of the components of FIG. 1;

FIG. 5-A is a side view exploded perspective of inlet control components for another embodiment the present technology;

DETAILED DESCRIPTION

Figure 1:
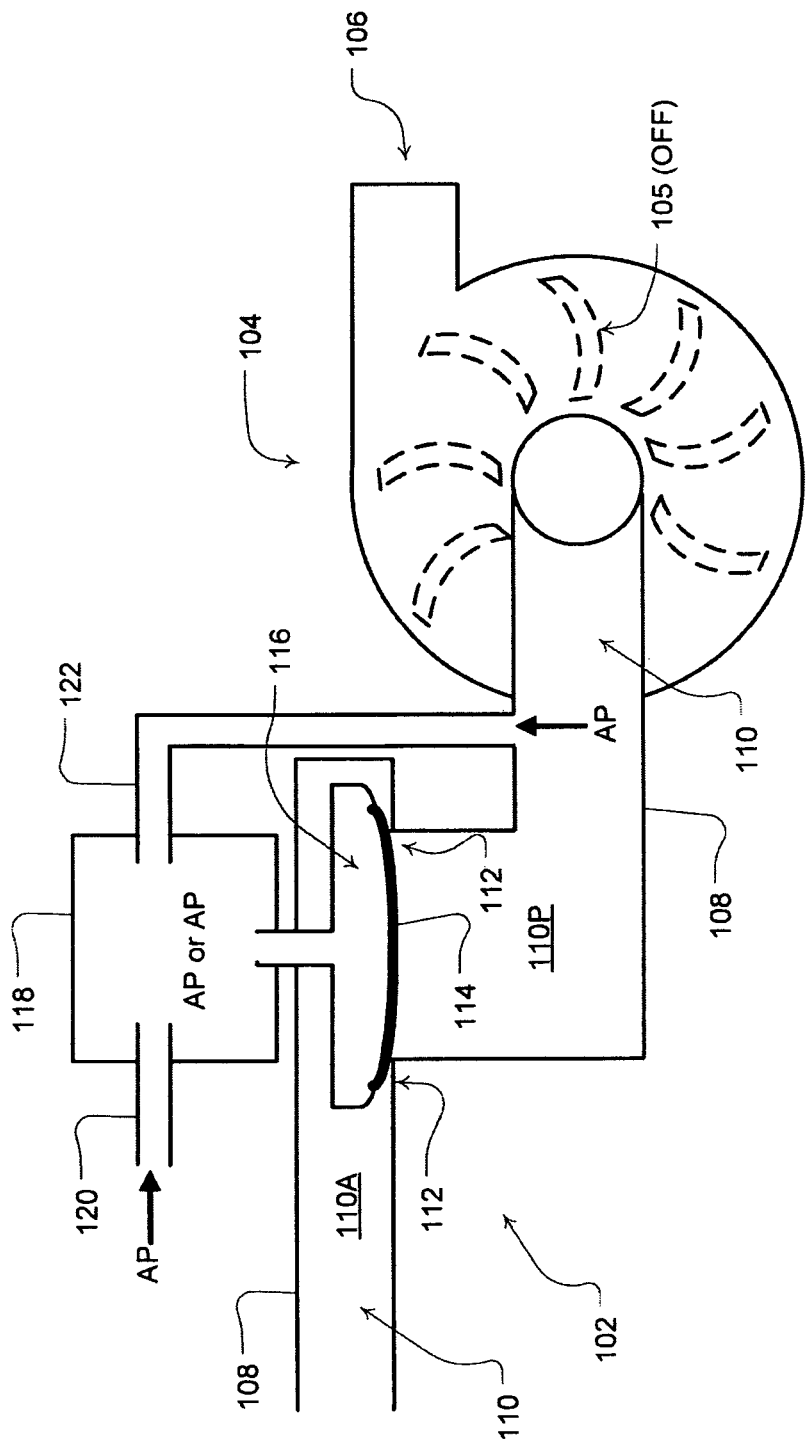
FIG. 1 is a schematic diagram illustrating components of an inlet control device for a flow generator in an embodiment of the present technology.

Example embodiments of the current technology may be implemented with a breathable gas inlet control device 102 for a flow generator or a respiratory treatment apparatus including components illustrated in the schematic diagram of FIG. 1. Typically, the flow generator, such as a servo-controller blower 104, will include a motor, volute and impeller 105. With the impeller 105, the blower can produce a flow of breathable gas (e.g., air) to the gas outlet 106. Although FIG. 1 illustrates a flow generator of the blower type, also known as a radial compressor, other flow generators may be utilized such as a piston based compressor. In a respiratory treatment apparatus, the gas outlet 106 will typically be configured for coupling with a patient interface for respiratory treatment such as a delivery or supply conduit and mask or tracheotomy tube (not shown).

The breathable gas can be drawn into the blower through a gas inlet 108 by powered rotation of the impeller. Rotation of the impeller 105 creates a lower gas pressure condition at the inlet and a higher gas pressure condition at the outlet relative to ambient or atmospheric pressure. The gas inlet can be formed by an inlet chamber 110 that serves as a path that directs, a flow of gas drawn into, the impeller 105. As shown in FIG. 1, an aperture 112 of the inlet chamber 110 may be sealed by an inlet flow seal 114. Controlled movement of the inlet flow seal 114 serves to impede flow by preventing or permitting gas transfer between an anterior portion 110A of the gas inlet chamber 110 exterior of the seal and a posterior portion 110P of the gas inlet 108 interior of the seal.

As illustrated, in FIG. 1, the inlet flow seal 114 is coupled to a cavity or seal activation chamber 116. Selective control of the gas pressure within the seal activation chamber serves to control the movement of the inlet flow seal 114. For example, the inlet flow seal 114 may be formed by a flexible membrane. The membrane may be formed and positioned to permit it to resiliently close or seal the aperture 112 under a normal pressure condition such as when an ambient pressure condition exists within the seal activation chamber 116 and in the gas inlet 108. As illustrated in the embodiment of FIG. 1, such a pressure condition may exist when the blower 104 is not operating. Moreover, depending on the resilience of the seal and/or the pressure condition in the seal activation chamber, the seal can prevent a back flow of gas from the posterior portion 110P of the inlet chamber 110 toward the anterior portion 110A of the inlet chamber 110. Thus, the inlet, flow seal may also operate as a non-return valve.

The cross-sectional area of the inlet flow seal 114 (i.e., the surface area of the seal) may be designed to be larger than the cress-sectional area of the gas passageway of the inlet aperture 112 as illustrated in FIG. 1-A. Consequently, the cross-sectional area ratio of the aperture to the inlet flow seal can be greater than 1:1, preferably between about 1:1.5 and about 1:3, more, preferably the ratio is about 1:2. In the example of FIG. 1-A, the surface area 115 of the seal 114 is about two times the cross-sectional area 113 of the gas passageway 112 of the inlet aperture (i.e., area ratio $AR_2/AR_1=\frac{1}{2}$).

In the embodiment of FIG. 1, a flow control valve 118, such as an electro-mechanical valve (e.g., a three port, two way valve), may be implemented to permit changes to the pressurization of the seal activation chamber 116. For example, as illustrated, the flow control valve 118 may be selectively set to permit the pressure of the seal activation chamber 116 to equalize with different pressures such as with an ambient pressure (illustrated in FIG. 1 as arrow "AP") through a first conduit 120 or another pressure of the inlet chamber 110 through a second conduit or the pressure communication conduit 122, such as the ambient pressure of the posterior portion 110P of the inlet chamber 110 when the blower is not operating.

Several operational modes of the apparatus of FIG. 1 will now be described with reference to FIGS. 2, 3, 3-A and 3-B.

Figure 2:
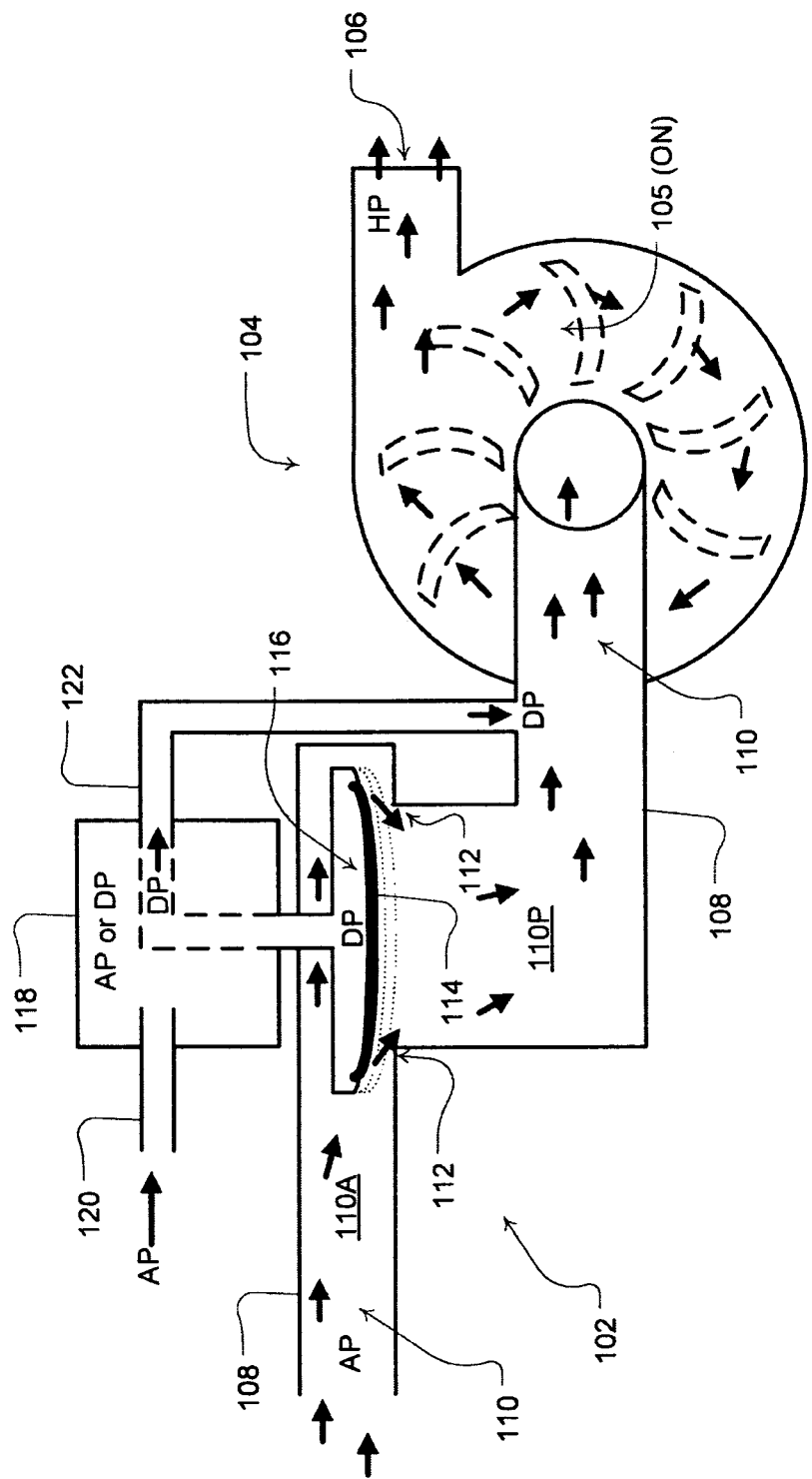
FIG. 2 is a schematic diagram illustrating, pressurized operation of the components of FIG. 1.

As illustrated in FIG. 2, a negative or decreased pressure relative to ambient pressure may exist within the posterior portion 110P of the inlet chamber 110. This negative pressure (illustrated in FIG. 2 as arrow "DP") may be communicated to the seal activation chamber 116 via the pressure communication conduit 122 by operation of the flow control valve 118. For example, as further illustrated in FIG. 2, when the blower is activated and the flow is directed towards the gas outlet 106, the flow control valve 118 may be set to permit pressurization of the seal activation chamber 116 at the negative pressure "DP" of the inlet chamber 110 caused by the pressure of the inwards flow of breathable gas such as when the patient inhales (i.e., inspiration). The pressure may be communicated to the seal activation chamber 116 through the pressure communication conduit 122 serving as a pneumatic link. Significantly, the seal activation chamber 116 and the inlet flow seal 114 may be configured to permit opening of the aperture 112 as a result of this change in pressure in the seal activation chamber 116. In this regard, the rotation of the impeller of the blower acts as a pressure source but the pressure drop in the posterior portion 110P of the inlet chamber 110 relative to the anterior portion 110A that opens the seal is a consequence of flow through the inlet chamber 110 rather than simply from the rotation of the impeller. For example, the flow through the posterior portion 110P may be controlled of induced by the breathing cycle of the patient whether or not the blower is powered. Moreover, as illustrated in more detail herein, in some states of the apparatus the blower may be powered (e.g., rotating) but there may be no flow through, the posterior portion 110P, such as when the output of the blower is blocked. Nevertheless, if patient flow exists, the impeller-induced pressure in conjunction with the patient's flow-induced pressure may both contribute to the level of pressure, that will exist in the posterior portion.

The size of the aperture 112 and the seal 114 as well as the flexibility of the seal can be chosen so that the decrease in pressure within the chamber retracts one or more portions of the seal into the seal activation chamber 116. This retraction may withdraw the seal 114 into the seal activation chamber 116 providing a gap between the anterior portion 110A of the inlet chamber 110 and the posterior portion 110P of the inlet chamber 110. This retraction of the seal will then permit gas flow between the seal and the aperture from the anterior portion 110A to the posterior portion 110P and then into the impeller.

Depending on the flexibility of the seal, the extent of the movement of the seal can be a function of the varying flow generated by the patient. Thus, the size of the opening formed by the aperture and the flexible seal during blower operation can be proportional to the induced flow as illustrated by the dotted lines in FIG. 2. For example, greater inwards flow in the posterior portion 110P of the inlet chamber can result in greater openings of the aperture 112 to allow more flow into the blower. Similarly, smaller inwards flow in the posterior portion 110P of the inlet chamber can result in smaller openings of the aperture 112 to allow less flow into the blower. The proportional opening permits the forming of a minimum necessary opening size sufficient to permit the desired flow drawn by the blower. Since larger openings can cause greater noise as the flow of gas passes across the opening, a potential benefit of such a proportional flow opening is a reduction of noise. Such a feature can be significant for a respiratory treatment apparatus designed for treatment of patients during sleep.

Thus, in some embodiments, the inlet control device may be implemented with a variable inlet opening to a How different levels of flow to be supplied during inspiration as required by the patient. During inspiration the seal acts as a passive proportional valve that adjusts its distance from a rim of the aperture 112 to implement a variable opening. The size of the opening then may be related to the level, of patient flow. In a particular example embodiment, a simple passive pneumatic (flow) servo control may be implemented as follows:

(a) at 0 flow, the valve is fully closed;
(b) at between approximately >0 and <70 L/min forward flow, the valve aperture size is linked to the flow;
(c) at approximately >70 L/min, the valve is fully opened with a fixed, aperture size.

However, other flow ranges may be configured. When compared to devices that have fixed inlet openings, such a variable opening can optimize the working conditions of the blower and/or decrease the noise radiating from the system.

Figure 3:
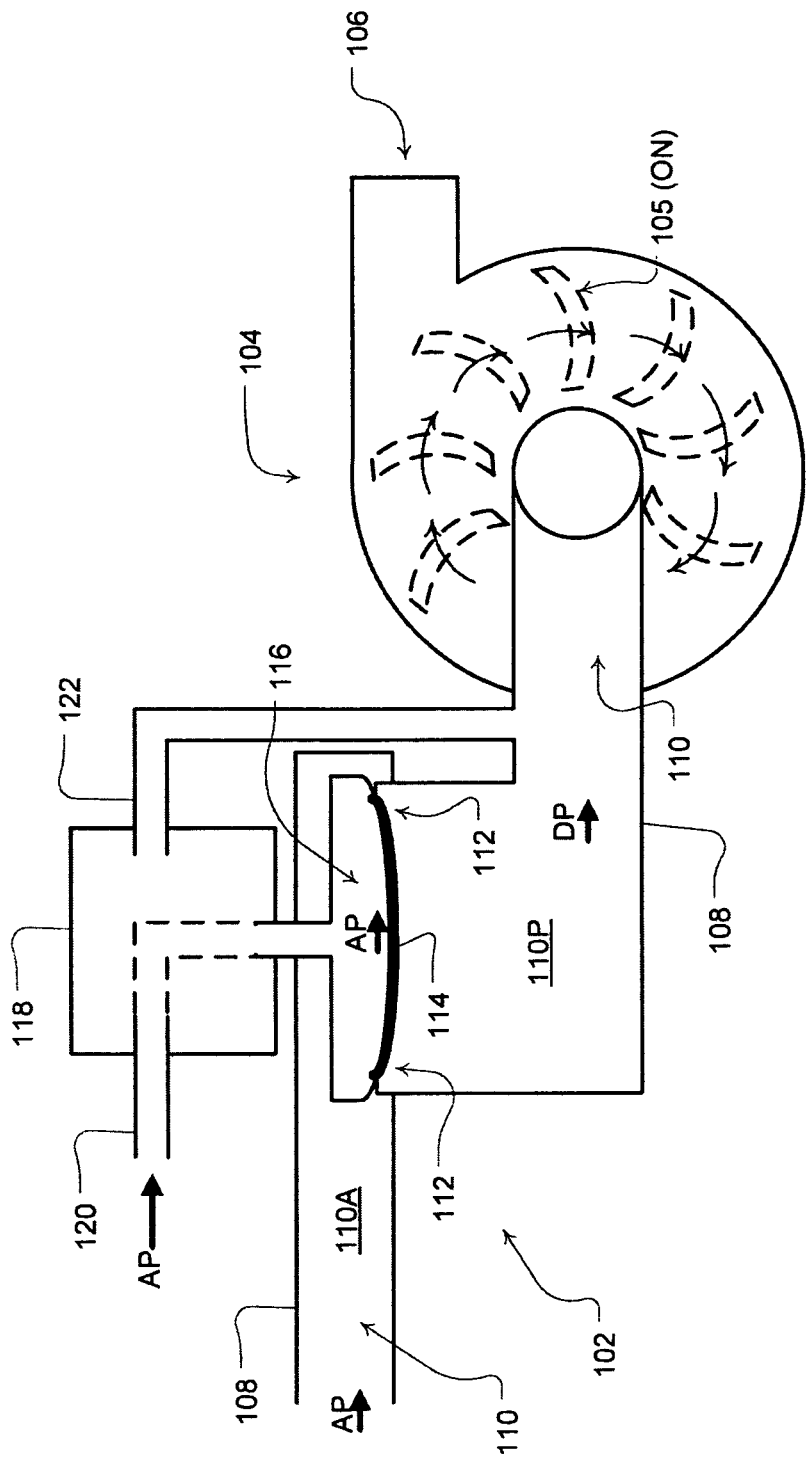
FIG. 3 is a schematic diagram illustrating de-pressurized operation of the components of/FIG. 1.

As further illustrated in FIG. 3, when the blower is activated, the flow control valve 118 may be set to relieve or discontinue the pressurization of the seal activation chamber 116 without necessarily also stopping or reducing the powered impeller rotation. For example, the flow control valve 118 may be set to communicate an ambient pressure to the seal activation chamber 116 through the first conduit 120 or pneumatic link. The resultant equalization in pressure in the seal activation chamber 116 can permit the inlet flow seal 114 to return to its normal configuration adjacent to the aperture 112 and thereby to seal the aperture 112. Moreover, in addition to the seal resilience, in the event that the blower is still operating (i.e., the impeller is still rotating) or the patient still inspiring as shown in FIG. 3, the decreased pressure condition in the posterior portion 110P of the inlet chamber 110 in relation to the higher ambient pressure condition in either of the anterior portion 110A of the inlet chamber 110 or the seal activation chamber 116 can further serve as a suction force to further enforce closing of the seal to the aperture 112.

Accordingly, the seal then can serve as an efficient and rapid means to prevent a flow of gas into the blower (i.e., shut off the inlet supply) without necessarily changing the speed of the blower or necessarily relying on braking of the motor of the blower. Avoidance of braking can reduce heat and keep the blower cooler. Avoidance or reduction of braking may also serve to reduce energy requirements of the system since less current may be required to operate the valves of the inlet flow control device when compared to supplying the current to the flow generator to control a reduction in blower speed.

Accordingly, in some example embodiments, the inlet control can be implemented to reduce pressures delivered by the blower during expiration with or without braking of the motor speed. It may also be implemented to more immediately stop and start generating flow from the blower. For example, a rapid stopping and starting of flow can be controlled by a controller using this device to then induce a percussive mode of breathing in a patient that may be suitable for causing secretion removal (e.g., inducing patient coughing).

Thus, the closing of the inlet control device 102 may serve as part of a control scheme for making controlled adjustments of the supplied treatment gas. For example, this reduction in size of the inlet aperture (e.g., closing) may be implemented to transition from an inspiration pressure to an expiration pressure without relying on a rapid deceleration of the blower. In this regard, the blower is unloaded by shutting off the flow (e.g., closing of the inlet control device 102). This means that the blower will decelerate more quickly and will not require the high levels of induced current normally required when braking a blower that is still receiving flow through the inlet. In other words, the blower does not have any load when it cannot draw air in through the inlet. Thus, the flow can be interrupted with a rapid response time due to this unloading of the blower. The ability to rapidly control the flow allows the shape of the respiratory treatment waveform produced by the flow generator to be more finely tuned. If a sharp pressure waveform/response is required then the inlet control device aperture can be closed rapidly.

In some other types of devices lacking the present technology, the transition from inspiration, to expiration can result in a flow spike at the beginning of expiration due to the time that is required for the blower to slow down. This flow spike can be avoided in embodiments of the present technology by the closing of the inlet control device and thereby shutting off inlet flow.

Thus, in some embodiments, the controller may detect an expiratory related condition (e.g., beginning of expiration, end of inspiration, etc.) from the sensors (e.g., a measure from a flow sensor) and set the valves of the inlet control device to close the inlet aperture and thereby interrupt flow to the flow generator. Optionally, the controller may also simultaneously or contemporaneously change a setting (e.g., reduce current) of the flow generator to, for example, reduce a speed of the flow generator to a setting suitable for generating a pressure appropriate for expiration (e.g., an expiratory pressure level). Such a controller change might also involve the setting of a flow generator used for generating a positive end expiratory pressure level (PEEP). Thus, the control of the inlet flow device, and optionally the flow generator, can also assist in implementing a desired shape of a generated respiratory treatment pressure waveform.

As illustrated, in FIG. 3-A, the blower may be activated while the flow control valve 118 may be set to equalize the pressure of the seal activation chamber 116 and the posterior portion 110P of the inlet chamber 110. Moreover, the output of the blower at or beyond the outlet 106 may be blocked (e.g., due to some problem of the patient interface or if the patient is neither inhaling nor exhaling) so as to prevent blower induced flow out of the outlet 106. During this operation, without patient flow, the seal 114 can remain in a position to close the aperture 112 due to the configuration of the seal and the equalized pressure of the seal activation chamber 116 and the posterior portion 110P of the inlet chamber 110, which will be approximately the same pressure as the anterior portion 110 of the inlet chamber 110.

Shutting off the flow also results in other benefits such as when it is implemented to prevent back flow with a non-vented mask system. For example, as illustrated in FIG. 3-B, the blower may be activated while the flow control valve 118 may be set to equalize the pressure of the seal activation chamber 116 and the posterior, portion 110P of the inlet chamber 110. In such a condition, a patient might expire so as to induce a back flow BF condition into the outlet 106 and thereby create a positive pressure (shown as "HP" in FIG. 3-B), relative to ambient, in the posterior portion 110P of the inlet chamber 110. However, in such a case, the seal 114 can remain in a position to close the aperture 112 and prevent the back flow due to the configuration of the seal and the equalized pressure of the seal activation chamber 116 and the posterior portion 110P of the inlet chamber 110, even though the positive pressure HP of the posterior portion 110P would exceed the ambient pressure in the anterior portion 110A of the inlet chamber 110.

The prevention of back flow can also have benefits for a system that utilizes oxygen. For example, when oxygen is injected after or downstream of the blower as discussed in more detail herein, shutting off the flow during expiration by closing the valve means that the oxygen may be maintained in the pressure side of the device (e.g., no oxygen escapes outside the device). Also this arrangement may reduce the exposure of the motor to oxygen as there is no or minimal oxygen backflow through the blower.

Figure 4:
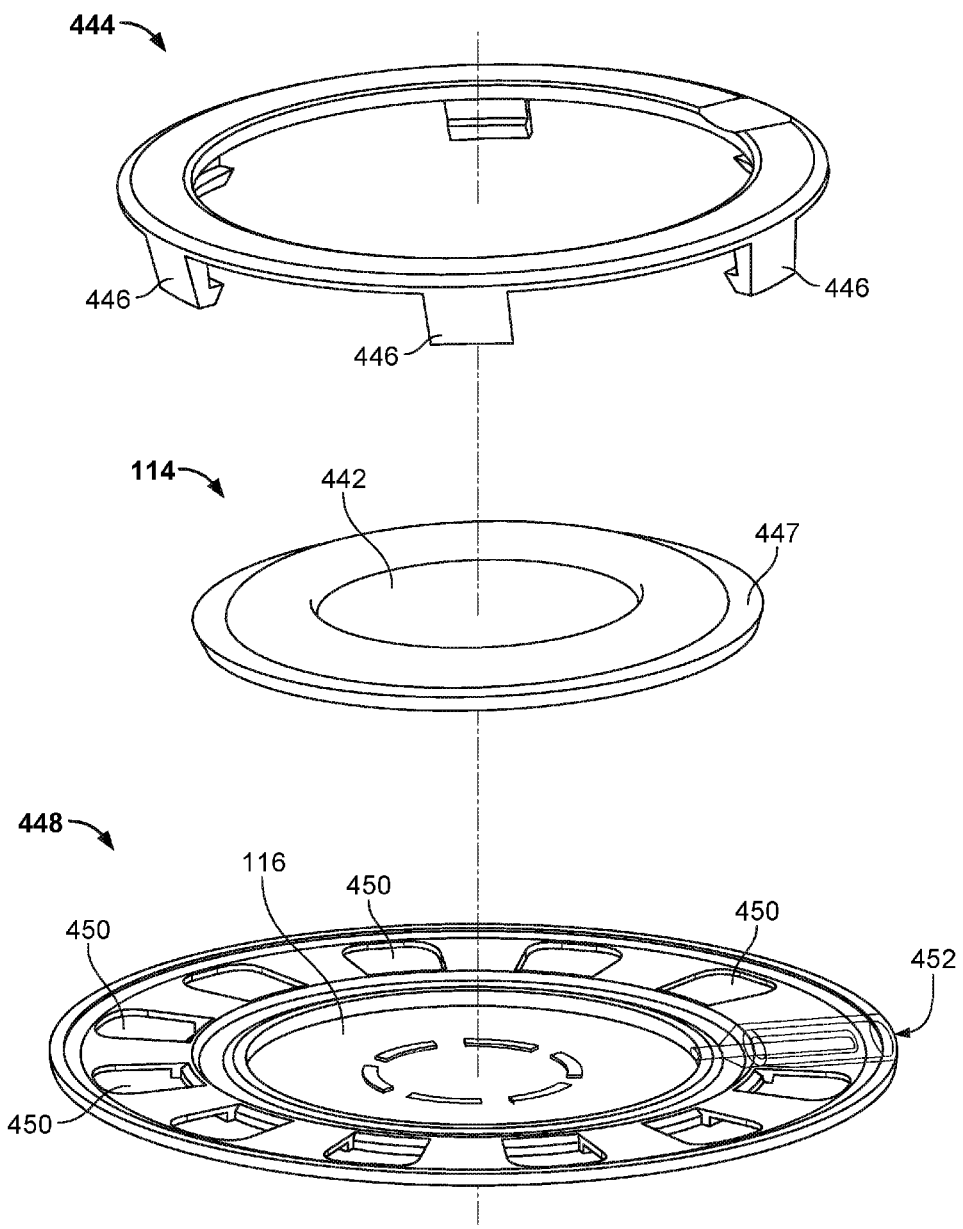
FIG. 4 is an illustration of example inlet control components for an assembly of the present technology.

Components of an example inlet control assembly are illustrated in FIG. 4. The inlet flow seal 114 is formed of a flexible material with a sealing surface 442. The sealing surface 442 serves as a membrane for plying against, an inlet aperture (not shown) as previously described. A clamp ring 444 having flexible prongs 446 is configured for clamping the outer perimeter lip 447 of the inlet flow seal 114 to a chamber body 448 to form the seal activation chamber 116 between the chamber body and the inlet flow seal. The chamber body 448 includes holes 450 to permit inlet airflow through the chamber body 448 around and externally of the seal activation chamber 116. Some of the holes may also be spaced and sized to receive the flexible prongs 446 of the clamp ring 444 when the prongs are snapped or engaged with the holes. The chamber body 448 includes a pressure port 452 for communicating the selected pressure from one or more flow control valves 118 (not shown in FIG. 4).

Figure 5:
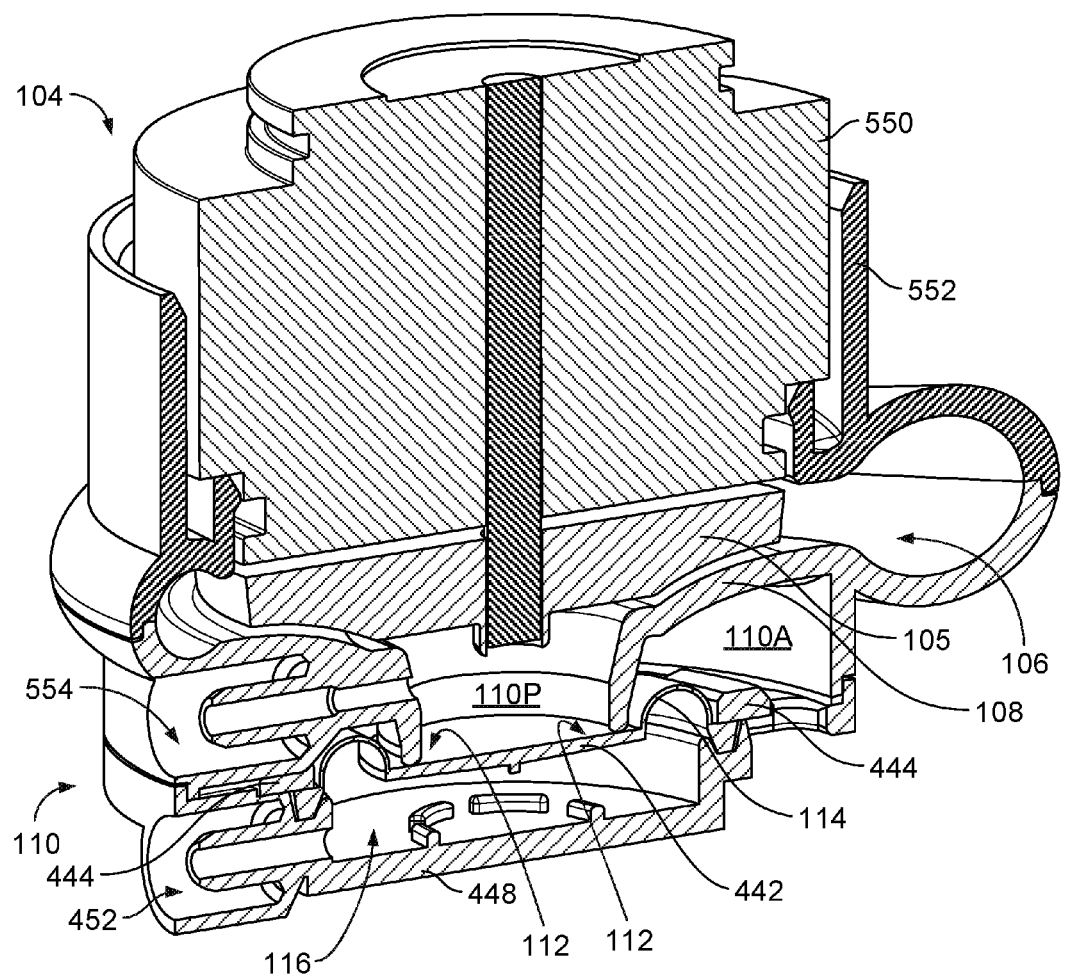
FIG. 5 is a side view cross-sectional illustration of example inlet control components of FIG. 4 installed on a volute housing of a blower in an embodiment of the present technology.

FIG. 5 contains a cross sectional illustration of the example inlet control assembly components coupled to a blower 104 or flow generator. The illustrated blower 104 includes the motor 550 and impeller 105 coupled to a volute 552 that serves as a housing for the impeller 105 of the flow generator. In this embodiment, the volute includes the flow inlet 108. When installed, the sealing surface 442 of the inlet flow seal 114 plies against the circumference of a rim of the flow inlet 108. During the operations previously discussed, the rim of the inlet 108 and the retraction of the sealing surface 442 forms an opening at the aperture 112. In this embodiment, the wall of the volute that serves as the inlet 108 includes a pressure port 554. The pressure port 554 of the inlet 108 permits an exchange of pressure between the posterior portion of the inlet chamber 110P and the seal activation chamber 116 through a conduit (not shown in FIG. 5) and the flow control valve 118 (also not shown in FIG. 5).

As illustrated in FIG. 5, the particular structure of this embodiment may have the potential for miniaturization. That is, its compact design can reduce the size of the housing of a respiratory treatment apparatus. In this regard, the location of the seal and seal activation chamber at the inlet and close to the blower can provide a reduction in space. In this regard, portions of the components of the inlet control device may be integrated with a volute for the blower. However, it is also possible in alternative embodiments to locate, the seal activation chamber, and seal elsewhere with respect to the apparatus or blower. For example, it may be attachable and/or removable to the blower or blower housing via a tube or other conduit (not shown).

Another embodiment of the inlet control assembly is illustrated in FIG. 5-A. In this embodiment, the inlet flow seal 114 is clamped between mounting ring 555 and chamber body 448. The mounting ring 555 is adapted for removable installation with the wall of the inlet chamber 110. For example, side clips or threads (not shown) of the mounting ring 555 may mate with receiving grooves (not shown) of the wall of the inlet chamber 110. When snapped or rotated in place, the mounting ring secures the inlet control assembly to the blower volute 552. In this example of the inlet control assembly, the mounting ring 555 includes flexible prongs 446 configured for clamping the outer perimeter lip 447 of the inlet flow seal 114 to the chamber body 448 to form the seal activation chamber 116 between the chamber body and the inlet flow seal. The chamber body 448 includes holes 450 to permit inlet airflow through the chamber body 448 around and externally of the seal activation chamber 116. Some of the holes may also be spaced and sized to receive the flexible prongs 446 of the mounting ring 555 when the prongs are snapped or engaged with the holes. The chamber body 448 includes the pressure port 452 for communicating the selected pressure from one or more flow control valves 118 (not shown in FIG. 4). Another pressure port 554 leading to the posterior portion 110P of the inlet chamber 110 is integrated into the volute at the wall of the inlet chamber.

Figure 5A:
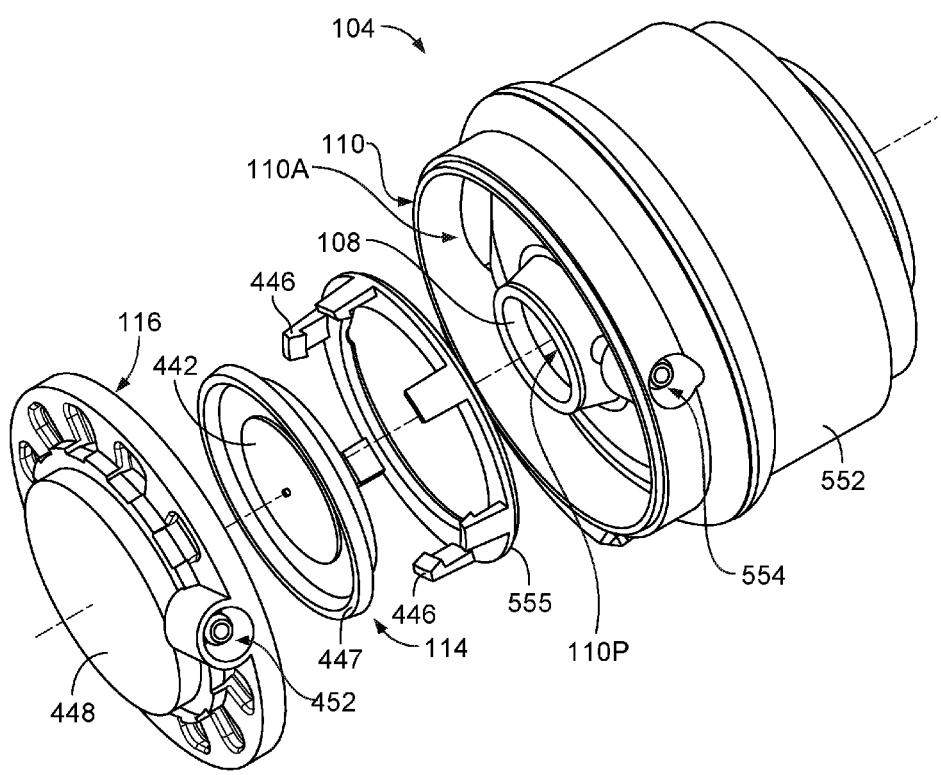

In the embodiments, of FIGS. 5 and 5A various arrangements are shown for coupling components of the inlet control to the housing of a blower or the inlet of a blower. However, additional configurations may also be implemented to achieve a connection with a blower. For example, some or all of the inlet control components may be configured as a removable unit or module. The unit or module may then be removably coupled to a portion of an inlet of a blower or housing thereof. For example, the unit or module may be configured with a bayonet connection or a bayonet coupler. Similarly, the unit, or module may be coupled to the inlet of a blower such that it mates with the inlet of the blower by an interference fit. Other coupling arrangements may also be implemented such as a snap-fit arrangement.

Example Respiratory Treatment Apparatus Operation

Figure 6:
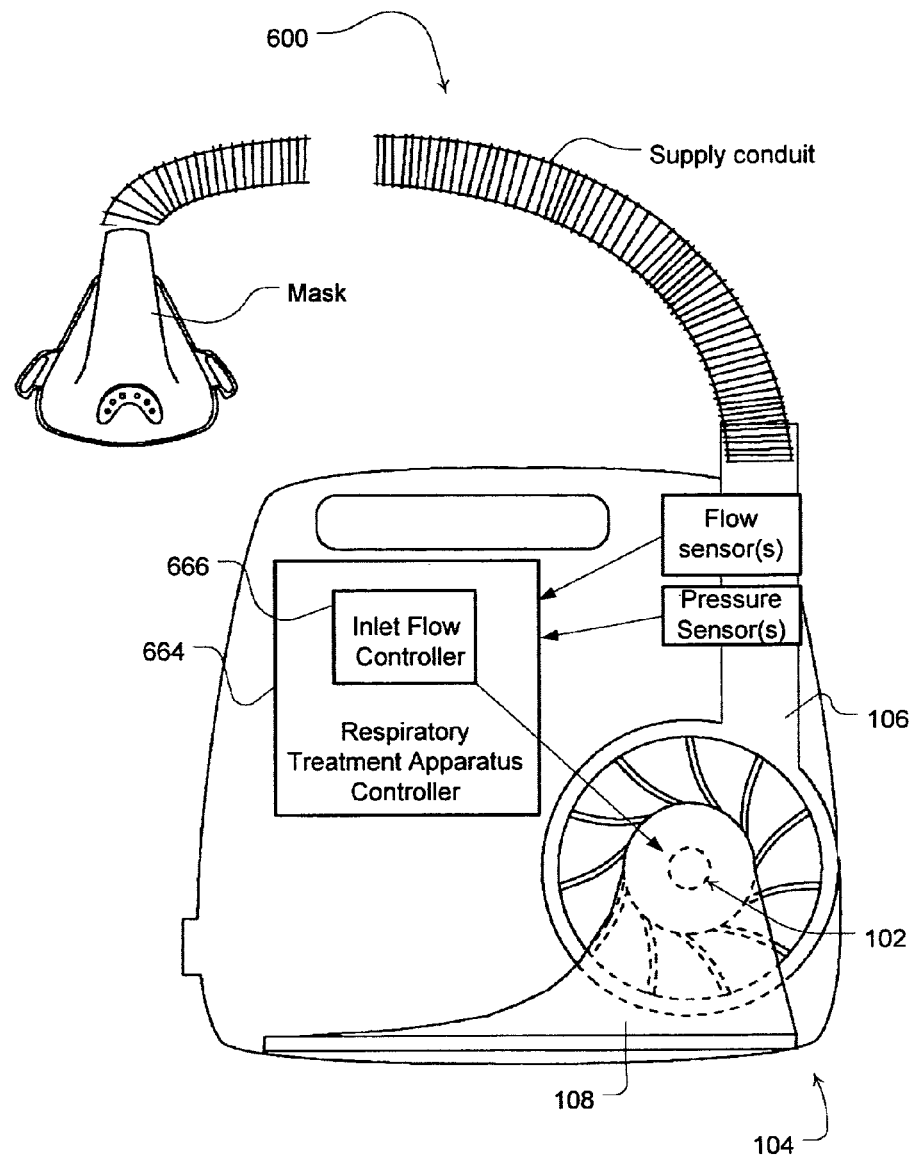
FIG. 6 is an illustration of example components of a respiratory treatment apparatus with an inlet controller of the technology.

As previously discussed, the breathable gas inlet control 102 device may be implemented, with the flow generator of a respiratory treatment apparatus 600, such as the ventilator or continuous positive airway pressure device illustrated in FIG. 6. Such an apparatus includes a controller 664, with one or more microcontrollers or processors, so that the respiratory treatment apparatus 600 may be configured with one more treatment regimes for setting the pressure delivered by the pressure generator or blower in conjunction with signals from optional pressure sensors(s) and/or flow sensor(s). Thus, the controller may adjust the speed of the blower during patient treatment to treat detected conditions (e.g., flow limitation, inadequate ventilation, apnea, etc.) and/or synchronize pressure changes during detected patient respiration to simulate or support respiration. In addition, the controller 664 may be configured to selectively set the pressure of the seal activation chamber 116 by control of one or more flow control valves 118 and thereby serve as an inlet flow controller 666 for permitting flow of gas (e.g., air or oxygen and air) to the blower and/or to prevent a back flow of gas from the blower. In this manner, the inlet flow controller 666 controls the inlet flow seal 114.

Thus, the controller 664 or inlet flow controller 666 will typically include one or more processors configured to implement particular control methodologies such as the algorithms described in more detail herein. To this end, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. The controller will also typically include a bus or electronic interface for setting the flow control valves as well as the other components of the apparatus (e.g., blower motor).

During operation of the respiratory treatment apparatus and depending on the desired usage, the inlet flow controller 666 may set the gas inlet control device 102 based on the detection of different conditions of the system. For example, from an analysis of pressure and flow data, the controller may set the gas control device 102 based on the detection of different states of the patient's respiratory cycle or enforcing those states such as inspiration, expiration, start of inspiration, start of expiration, inspiratory peak flow, inspiratory pause, etc. Known methods for the detection of these conditions from pressure and/or flow data or for enforcing them (e.g. timed backup breathing rates) may be implemented by the programming or the circuits; of the controller. Various examples of the setting of the gas inlet control device 102 by a controller in different system configurations and respiratory states are illustrated in FIGS. 7 through 15.

In the respiratory apparatus configuration of FIGS. 7 through 15 an additional flow control valve 772 (or pressure relief valve) is added under the control of the inlet flow controller 666. The additional flow control valve 772 selectively permits (a) an equalization of pressure or flow between the outlet 106 of the blower 104 and the anterior portion 110A of the inlet chamber 110 through back flow conduit 779 or (b) an equalization of pressure or flow between first conduit 120 to the first control valve 118 and the anterior portion 110A of the inlet chamber 110. However, in some embodiments, the optional back flow conduit 779 may not be present. In such a case, the port of the flow control valve 772 for the optional back flow conduit 779 may be capped such that the flow control valve 772 serves only as a 2-way valve able to selectively conduct gas between the inlet 108 and the first conduit 120. Optionally, the flow control valve 772 may be replaced by a 2-way valve.

Figure 7:
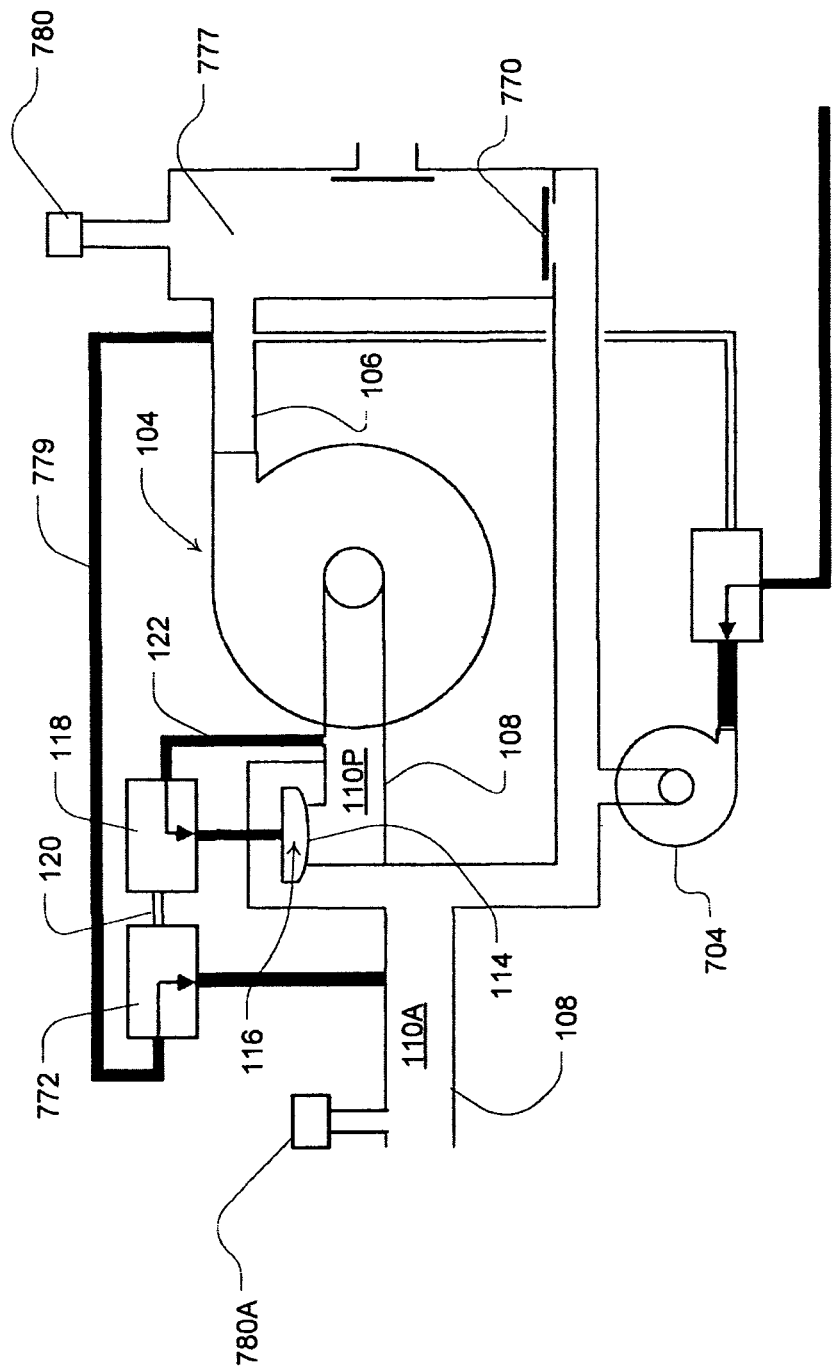
FIG. 7 is a schematic diagram illustrating components of an inlet control device for a flow generator in a further respiratory treatment apparatus embodiment of the technology.

In the example of FIG. 7, the flow control valve 772 can be implemented with a normal state that permits equalization of pressure or permits flow between the outlet 106 of the blower 104 and the anterior portion 110A of the inlet chamber 110. Such a recirculation of flow from the outlet of the blower 106 to the anterior portion 110A of the inlet chamber 110 may assist with cooling of the motor and may provide better control of the valve at low flows. Upon activation by the controller 666, the flow control valve 772 may then be switched to equalize pressure or permit flow between first control valve 118 via first conduit 120 and the anterior portion 110A of the inlet chamber 110. Similarly, the flow control valve 118 may be implemented with a normal state that permits equalization of pressure or permits flow between the posterior portion 110P of the inlet chamber 110 and the seal activation chamber 116. Upon activation by the controller 666, the flow control valve 118 may then be switched to equalize pressure or permit flow between the first conduit 120 and the seal activation chamber 116. In this case, the pressure of the seal activation chamber 116 is further dependent on the setting of the flow control valve 772. For example, when the flow control valve 118 is in its activated state and the flow control, valve 772 is in its normal state, the seal activation chamber 116 will effectively be sealed at the last pressure previously applied. Such a case may permit the seal activation chamber 116 to "lock" the inlet flow seal 114 open if a negative pressure condition existed in the seal activation chamber 116 prior to the activation of the flow control valve 118. In such a case, the inlet flow seal may be open even upon deactivation of the blower.

Additionally, in the example system of FIGS. 1 through 15, a second blower or positive end expiratory pressure (PEEP) blower 704 may also be included to deliver a positive pressure at the end of patient expiration. Although it is illustrated, the full operations of the PEEP blower 704 are beyond the scope of the explanation of the gas inlet control device 102 of the present technology. Also shown in the diagram is a safety valve 770 in a muffler chamber 777. Generally, the safety valve will be open during patient inspiration and closed during patient expiration.

Operations will now be described with reference to FIGS. 7 to 10. Generally, FIGS. 7 to 10 illustrate operations for vented ventilation (i.e., use of the apparatus with a vented patient interface or mask) to the extent that these figures may show an active or powered controller (i.e., turned on). FIG. 7 is a block diagram illustrating the default setting of the gas inlet control device 102 when the respiratory treatment apparatus is off the default setting shown in FIG. 7 is the same whether a vented or non-vented mask is utilized. In this state the flow control valve 772 and flow control valve 118 are not active (i.e., they are in their normal states).

FIG. 7 also illustrates the settings of the gas inlet control device 102 when the controller 664 implements a ventilation pause such as when the controller detects that the patient's expiration is complete and inspiration has not yet started. Thus, there is no or very low flow. The controller 664 does not activate either flow control valve 772 or flow control valve 118. While the blower may or may not be powered and it may be rotating in either case, the gas inlet control device 102 could be closed so as to prevent back flow from the blower to the anterior portion 110A of the inlet chamber 110.

Figure 8:
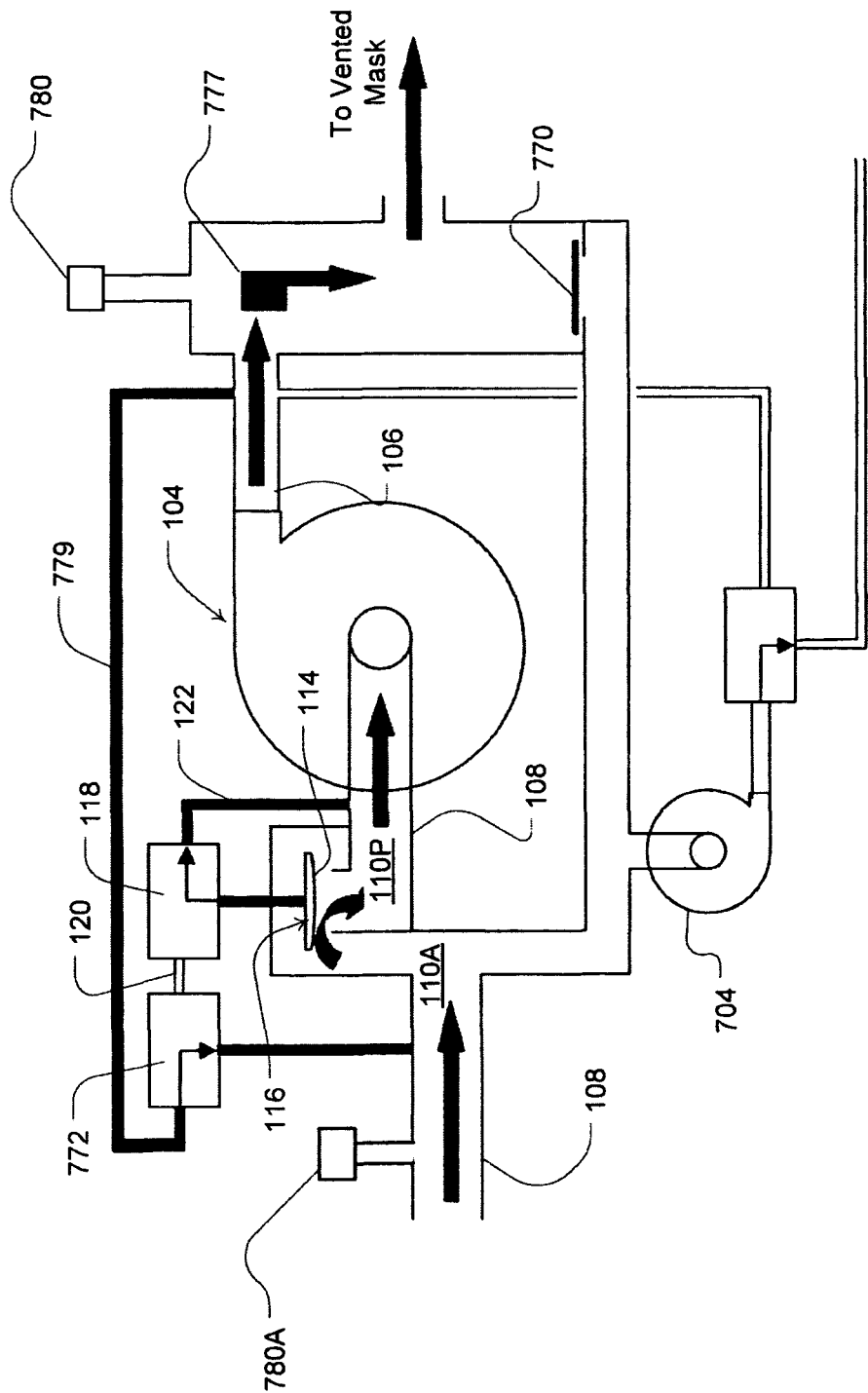
FIG. 8 is a schematic diagram illustrating operation of the components of the embodiment of FIG. 7 in an initial inspiration state.

FIG. 8 is a block diagram illustrating the setting of the gas inlet control device 102 when the respiratory treatment apparatus is on and the controller 664 implements the start of inspiration by either detection of patient inspiration or initiation of a timed backup. The controller 664 does not activate either flow control valve 772 or flow control valve 118. Since in this condition the blower would be powered to deliver an inspiratory positive airway pressure (IPAP), the patient's high inspiratory flow would generate a negative pressure condition or suction in the posterior portion 110P of the inlet chamber and the seal activation, chamber 116. Thus, the gas inlet control device 102 would be open to permit flow to the blower. Additionally, in this configuration, the flow from the outlet 106 through the back flow conduit 779 to the inlet chamber can serve a cooling function. With the leak flow created with the back flow conduit, the blower may run at a higher speed. By allowing greater flow through the blower it can serve to cool the blower.

Figure 9:
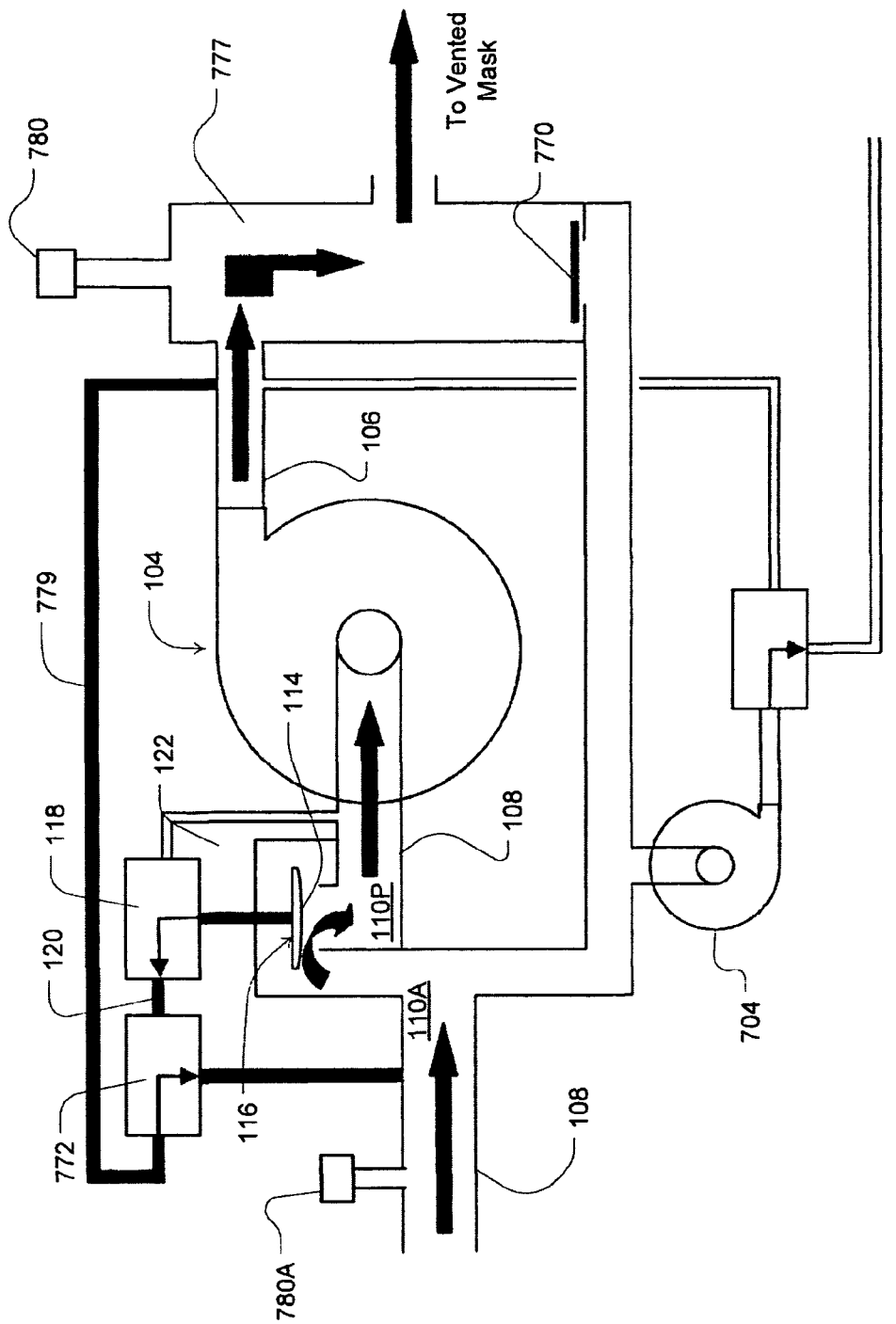
FIG. 9 is a schematic diagram illustrating operation of the components of the embodiment of FIG. 7 in a maximum inspiratory flow state.

FIG. 9 is a block diagram illustrating the setting of the gas inlet control device 102 when the respiratory treatment apparatus is on and the controller 664 detects the expected peak flow of patient inspiration. The controller 664 does not activate flow control valve 772 but does activate flow control valve 118. In this condition the blower would be powered to deliver an inspiratory positive airway pressure (IPAP). The generated negative pressure condition in the posterior portion 110P of the inlet chamber would then be maintained or sealed in the seal activation chamber 116 due to the activation of flow control valve 118. Thus, the gas inlet control device 102 would be "locked" open or at least partially open (depending on the amount of patient flow at the time of the activation of flow control valve 118) still permitting flow to the blower.

Figure 10:
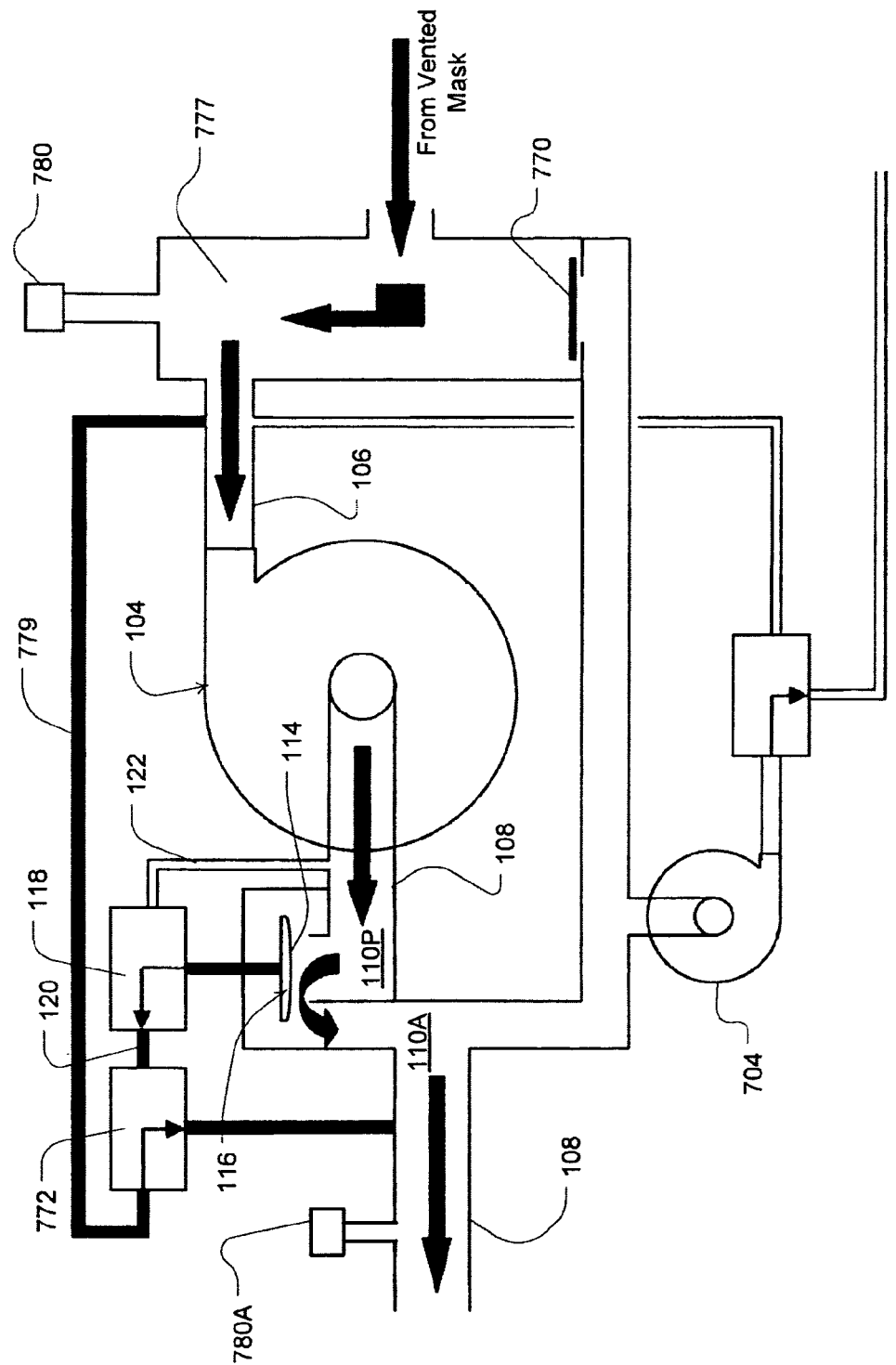
FIG. 10 is a schematic diagram illustrating operation of the components of the embodiment of FIG. 7 in an expiratory state.

FIG. 10 is a block diagram illustrating the setting of the gas inlet control device 102 when the respiratory treatment apparatus is on and the controller 664 detects patient expiration after the above inspiration. The controller 664 does not activate flow control valve 772 but does continue to activate flow control valve 118. In this, condition the blower would be powered to deliver an expiratory positive airway pressure (EPAP). Since the previously generated negative pressure condition is maintained or sealed in the seal activation chamber 116, the gas inlet control device 102 would be "locked" open or partially open. This would permit back flow from the outlet 106 through the blower and back out the inlet 108 to permit the patient's expiration flow to be vented through the respiratory treatment apparatus.

Figure 11:
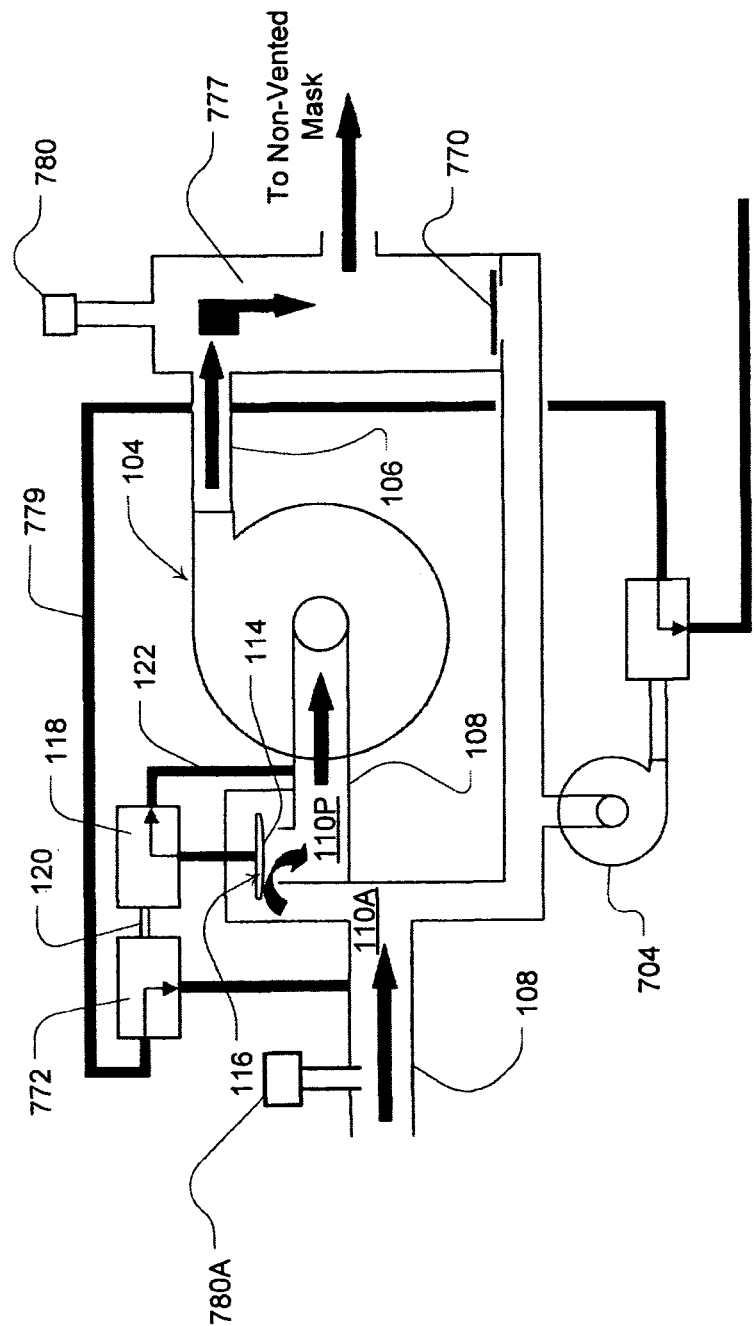
FIG. 11 is a schematic diagram illustrating operation of the components of the embodiment of FIG. 7 in an inspiratory state for a non-vented respiratory treatment apparatus.

FIGS. 11 to 15 illustrate operations for non-vented ventilation (i.e., use of the apparatus with a non-vented patient interface or mask). In this regard, FIG. 11 is a block diagram illustrating the setting of the gas inlet control device 102 when the respiratory treatment apparatus is on and the controller 664 implements the start of inspiration by either detection of patient, inspiration or initiation of a timed backup. The controller 664 does not activate either flow control valve 772 or flow control valve 118. Since in this condition the blower would be powered to deliver a flow or pressure based on a set point of a closed loop control as a result of the patient's inspiratory flow, there would be generated a negative pressure condition in the posterior portion 110P of the inlet chamber and the seal activation chamber 116. Thus, the gas inlet control device 102 would be open to permit flow to the blower. Additionally, in this configuration, the flow from the outlet 106 through the back flow conduit 779 to the inlet chamber can serve a cooling function.

Figure 12:
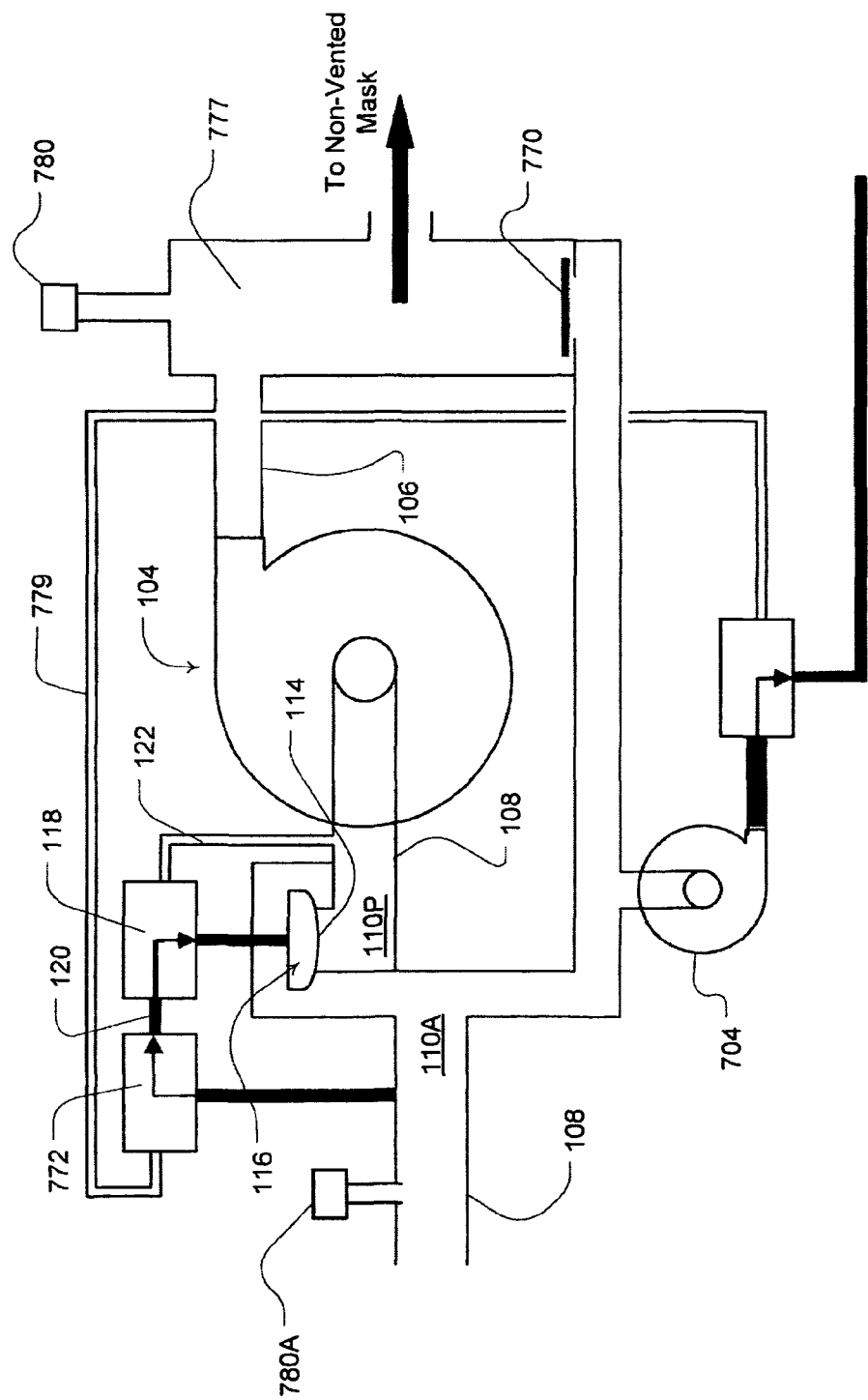
FIG. 12 is a schematic diagram illustrating operation of the components of the embodiment of FIG. 7 in an initial expiratory state, for a non-vented respiratory treatment apparatus.

FIG. 12 is a block diagram illustrating the setting of the gas inlet control device 102 when the respiratory treatment apparatus is on and the controller 664 detects the start of patient expiration (e.g., by detecting a peak flow threshold). The controller 664 activates both flow control valve 772 and flow control valve 118. In this condition the controller may de-power the blower. Since the seal activation chamber 116 has an ambient condition of the anterior portion 110A of the inlet chamber 110 as a result of the flow path through both flow control valve 772 and flow control valve 118, the gas inlet control device 102 would be closed. The closing of the inlet flow seal and stopping of any inlet flow would then tend to slow the natural inertia of the impeller of the de-powered blower like a brake.

Figure 13:
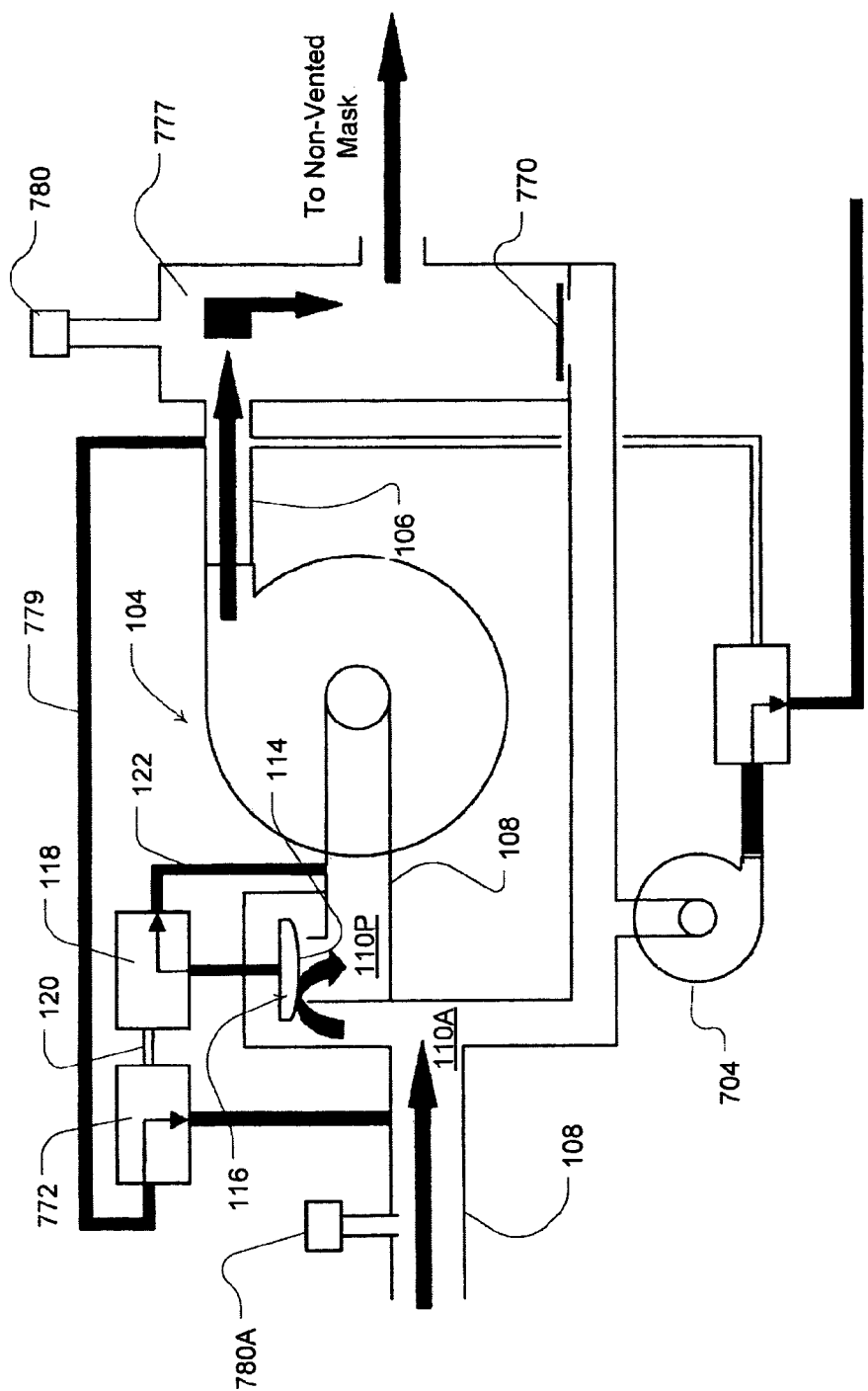
FIG. 13 is a schematic diagram illustrating operation of the components of the embodiment of FIG. 7 in an expiratory state for a non-vented respiratory treatment apparatus.

FIG. 13 is a block diagram illustrating the setting of the gas inlet control device 102 when the respiratory treatment apparatus is on and the controller 664 detects expiration. Flow-by control may be implemented. Flow-by control, is control of the seal during expiration to allow a very low level of flow through the inlet to compensate for leak (e.g., 1-2 liters) at the patient interface. The controller 664 does not activate either flow control valve 772 or flow control valve 118. In this condition the controller may minimally power the blower for generating a low level of flow based on a flow set point of a flow control loop. Since the seal activation chamber 116 has a negative pressure condition from the posterior portion 110P of the inlet chamber 110 as a result, of the flow path through the flow control valve 118, the gas inlet control device 102 would be partially open. The partial opening of the inlet flow seal would then permit a low flow of breathable gas through the blower to the outlet 106.

Figure 14:
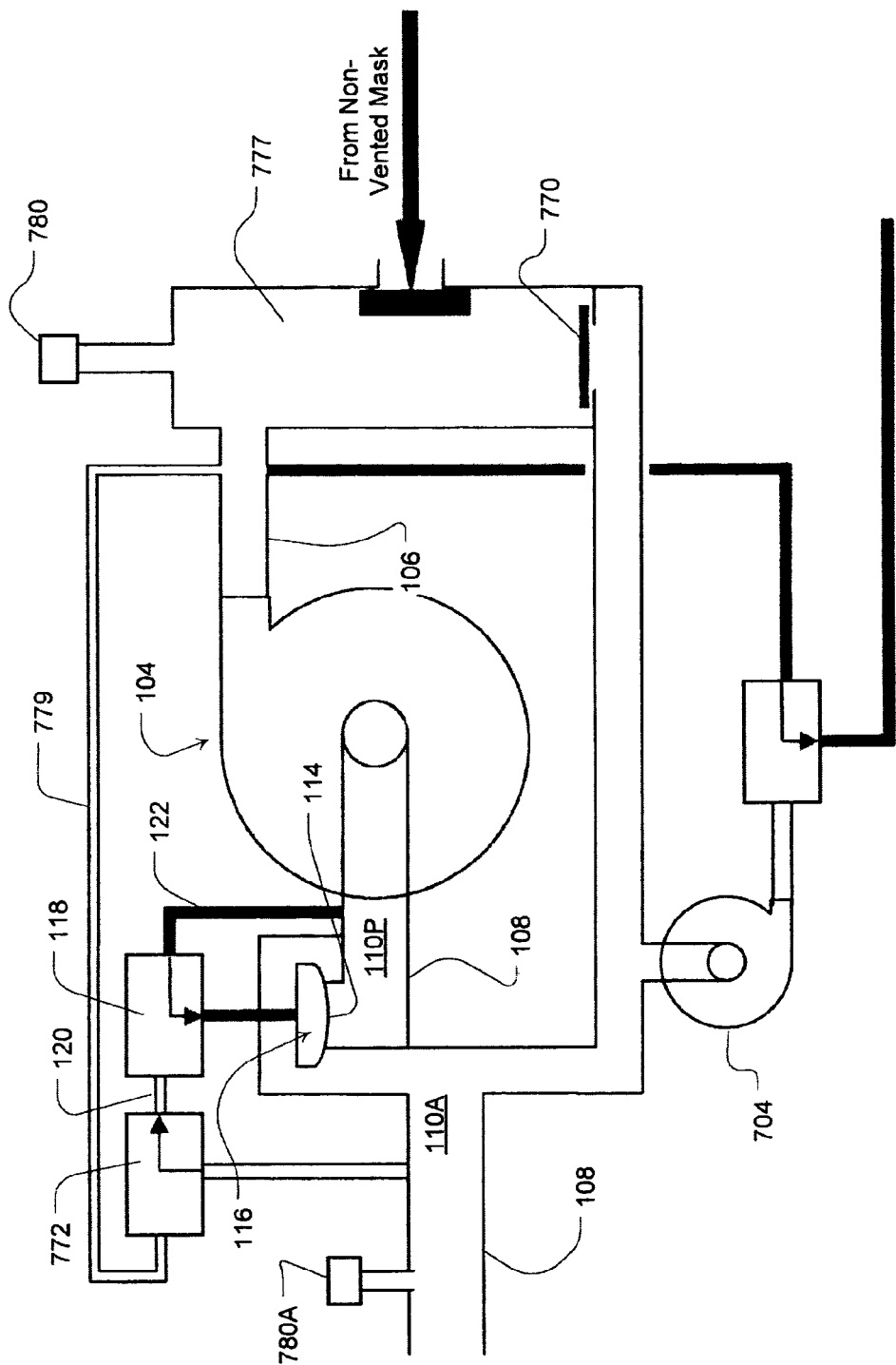
FIG. 14 is a schematic diagram illustrating operation of the components of the embodiment of FIG. 7 in an inspiratory pause state for a non-vented respiratory treatment apparatus.

FIG. 14 is a block diagram illustrating the setting of the gas inlet control device 102 when the respiratory treatment apparatus is on and the controller 664 detects an inspiratory pause or plateau. It may also be implemented for an automated positive end expiratory pressure (PEEP) measurement mode. The controller 664 activates, flow control valve 772 but does not activate flow control valve 118. In this condition the blower would be powered at a minimum speed. Due to the absence of patient flow, the gas inlet control device 102 would be closed. Moreover, the flow back conduit 779 would also be closed as a result of the setting of the flow control valve 772. Thus, flow back into the respiratory treatment apparatus from the patient interface or mask would be prevented.

Figure 15:
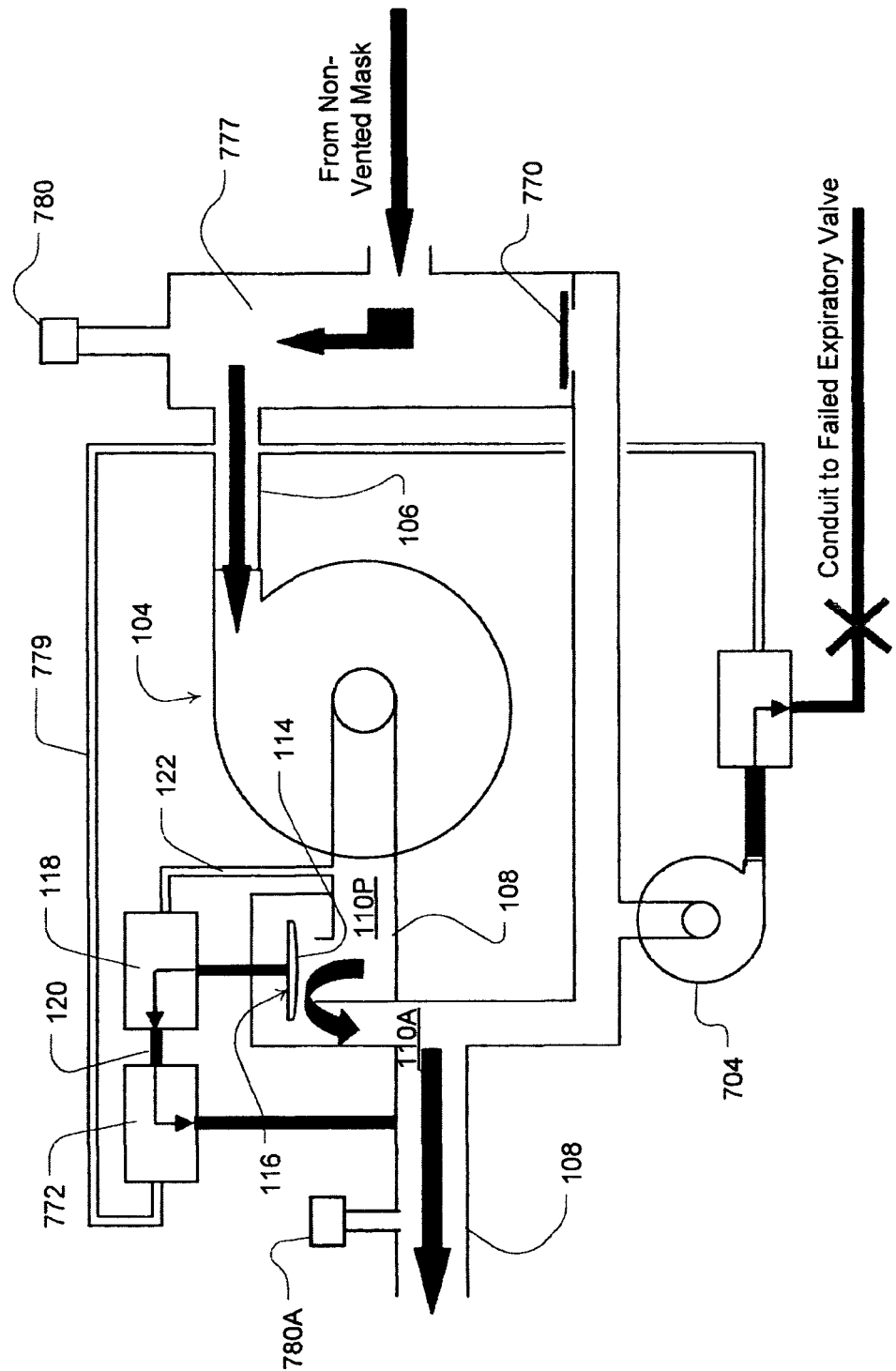
FIG. 15 is a schematic diagram illustrating operation of the components of the embodiment of FIG. 7 in a failure state for a non-vented respiratory treatment apparatus.

FIG. 15 is a block diagram illustrating the setting of the gas inlet control device 102 for a failure mode when the respiratory treatment apparatus is or and the controller 664 detects that the expiratory valve associated with the venting of the patient interface or mask is blocked, preventing patient exhalation during expiration. Upon detection of this condition, the controller 664 activates both flow control valve 772 and flow control valve 118. In this condition, equalization of pressure of the seal activation chamber 116 and the anterior portion 110A of the inlet chamber 110 is permitted. The blower would also be powered to a minimum speed. The patient's expiratory flow would then be sufficient to force open the inlet flow seal 114 as a result of the positive pressure created in the posterior portion 110P of the inlet chamber 110. Thus, the gas inlet control device 102 would be opened. Thus, flow back into the respiratory treatment apparatus from the patient interface or mask would be permitted.

In some embodiments, a supply of oxygen may also be mixed with the air supply to form the mixed breathable gas at the outlet. The oxygen may be injected in the flow path either downstream or upstream of the blower. For example, in some embodiments, the oxygen may be supplied or injected into the flow path at the outlet 106 as indicated by oxygen supply or oxygen inlet port 780 in FIGS. 7-15. For example, a high flow valve may be implemented to inject the oxygen. Injecting the oxygen after the blower and the valve also assists in preventing the oxygen from escaping back through the system and to atmosphere. This may reduce wastage of oxygen. Furthermore, injecting the oxygen after the blower prevents or limits the exposure of the blower and motor to the flammable oxygen, making the device safer. In alternative versions of the apparatus, the oxygen may be inserted or injected into the inlet 108 or inlet chamber 110. This may optionally be injected either in the anterior portion 110A or posterior portion 110P. Thus, the ambient air and oxygen mix would then flow through the blower and be pressurized by the blower at the outlet 106. This may be implemented by including a gas input port in the wall of the inlet 110. This option is illustrated, in FIGS. 7-15 as alternative oxygen supply or oxygen inlet port 780A. The oxygen may then be regulated with a valve at the gas input port. For example, the valve may regulate a low flow of oxygen with the ambient air. The apparatus may include oxygen port 780 near the outlet or oxygen 780A near the inlet, or both oxygen ports 780 and 780A to allow a choice of which oxygen port to use. However, generally in use only one of oxygen ports 780 or 780A are utilized.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

For example, as an alternative to the variable opening provided by the flexible seal as herein discussed, other components may be implemented as a variable opening and may also serve to reduce the level of noise radiated from the system. In this regard, some embodiments of the technology may implement an electrically controlled or electro-magnetic control system to vary the size of an opening at the inlet. Such a control system (e.g., a processor, a sensor and an electro-magnetic valve coupled together for signaling purposes) that measures flow and links or associates the required inspiratory flow to control signals for setting of the opening/closing size of a valve with variable sizes may be implemented. Thus, in such an embodiment, the inlet supply of gas to the blower would traverse through the valve and the aperture of the valve through which the gas traverses would have various sizes, that may be mechanically set/controlled. Optionally, the valve of such an alternative variable inlet control system may be implemented with a solenoid valve, mechanically controlled disk or mechanical controlled plunger that may move to form the variable opening. Advantageously in such embodiments the opening and closing of the valve may also be controlled/sized during expiration to provide a proportionally controlled non-return valve to more accurately control the shape of the respiratory waveform. For example, upon detecting a condition of expiration by a controller of the valve, the opening size of the valve may be set as a function of the detected expiratory flow. Such a system may be more expensive and may take up more space within a respiratory treatment apparatus when compared to the flexible seal version previously described.

The invention claimed is:

1. A respiratory treatment apparatus configured to provide a supply of pressurized breathable gas to a patient in successive respiratory cycles, each cycle of the successive respiratory cycles including an inspiration phase and an expiration phase, said apparatus comprising:
   a gas inlet;
   a gas outlet;
   a flow generator adapted to receive an inlet flow of breathable gas from the gas inlet and to pressurize the breathable gas prior to delivery to the gas outlet; and
   a controller adapted to control a level of pressure generated by the flow generator to provide an inspiratory pressure and an expiratory pressure, wherein during at least a portion of the expiration phase of said each cycle, the inlet flow to the flow generator is interrupted to facilitate a reduction in pressure from the inspiratory pressure to the expiratory pressure, wherein the controller is configured to interrupt the inlet flow by setting one or more electro-mechanical valves, wherein the apparatus further comprises a flexible seal in a flow path of the gas inlet and a seal activation chamber proximate to the flexible seal, wherein the setting of the one or more electro-mechanical valves controls a pressure level of the seal activation chamber.

2. The apparatus of claim 1 wherein the interruption of the inlet flow unloads a blower of the flow generator.

3. A flow generator for a respiratory treatment apparatus comprising:
a motor;
an impeller coupled with the motor;
a housing for the impeller comprising a volute, a gas inlet, a pressure communication conduit and a gas outlet, the gas outlet being adaptable for a conduit of a patient interface to deliver breathable gas as a respiratory treatment;
an inlet flow seal positioned to selectively open and close the gas inlet, the inlet flow seal having a first side internally proximate to an inlet chamber of the gas inlet and the inlet flow seal having a second side externally proximate to the inlet chamber of the gas inlet;
a seal activation chamber configured proximate to the second side of the inlet flow seal to permit a negative pressure in the seal activation chamber to open the gas inlet to a flow of breathable gas; and
a first flow control valve coupled with the pressure communication conduit, the first flow control valve being configured to selectively open and close the seal activation chamber to atmospheric pressure;
wherein the pressure communication conduit is configured to connect the inlet chamber and the seal activation chamber for pressure communication such that a change in pressure in the inlet chamber changes the pressure in the seal activation chamber.

4. The flow generator of claim 3 wherein the change in pressure in the inlet chamber is a decrease associated with a patient induced flow of breathable gas from the gas inlet to the gas outlet.

5. The flow generator of claim 4 wherein the decrease in pressure in the seal activation chamber is discontinued when the first flow control valve is set to open the seal activation chamber to atmospheric pressure and wherein the discontinued decrease in pressure permits closure of the gas inlet to a flow of breathable gas.

6. The flow generator of claim 3 wherein, when the first flow control valve is set to permit equalization between the seal activation chamber and the inlet chamber, a back flow from the gas outlet to the gas inlet increases pressure in the inlet chamber and the seal activation chamber such that the increase in pressure permits closure of the gas inlet and whereby the back flow is stopped.

7. The flow generator of claim 3 wherein the inlet flow seal comprises a flexible membrane.

8. The flow generator of claim 7 wherein the gas inlet comprises an aperture that is sealable by the inlet flow seal and wherein a surface area of the inlet flow seal is greater than an aperture area of the aperture.

9. The flow generator of claim 3 further comprising a second flow control valve coupled with the first flow control valve, wherein the second flow control valve is configured to selectively open and close the gas inlet to pressure of the gas outlet.

10. The flow generator of claim 9 wherein the first and second flow control valves are configured to selectively seal a pressure level within the seal activation chamber such that the seal activation chamber discontinues equalizing with a pressure of the inlet chamber and an ambient pressure.

11. The flow generator of claim 10 wherein the second flow control valve is configured to selectively open and close a path to the first flow control valve to equalize with ambient pressure of the gas inlet and the first flow control valve is configured to selectively open and close the seal activation chamber to the second flow control valve.

12. The flow generator of claim 10 further comprising: a controller configured to set the first flow control valve in response to a detection of a condition of inspiration to permit equalization of pressure in the seal activation chamber with pressure of the inlet chamber so as to permit an inspiratory flow to open the gas inlet.

13. The flow generator of claim 12 wherein the controller is configured to set the first flow control valve in response to a detection of a condition of expiration to discontinue a decrease in pressure in the seal activation chamber to close the gas inlet to a flow of breathable gas.

14. The flow generator of claim 13 wherein the controller is further configured to set the first flow control valve and the second flow control valve in response to a detection of a condition of inspiration to seal a pressure in the seal activation chamber and to lock open the gas inlet to permit a back flow of breathable gas.

15. The flow generator of claim 3 further comprising an oxygen input port coupled to the gas inlet to allow injection of oxygen gas into the gas inlet.

16. The flow generator of claim 3 further comprising an oxygen input port coupled to the gas outlet to allow injection of oxygen gas into the flow of breathable gas.

17. A respiratory treatment apparatus comprising:
a flow generator to produce a breathable gas at a pressure above atmospheric pressure for a pressure therapy regime, the flow generator comprising a gas inlet and a gas outlet, the gas outlet being adaptable for a conduit of a patient interface to deliver the breathable gas;
a controller to control the flow generator to produce the breathable gas according to a pressure therapy regime;
an inlet flow seal positioned to selectively open and close the gas inlet, the inlet flow seal having a first side internally proximate to an inlet chamber of the gas inlet and the inlet flow seal having a second side externally proximate to the inlet chamber of the gas inlet;
a seal activation chamber proximate to the second side of the inlet flow seal wherein a negative pressure in the seal activation chamber permits opening of the gas inlet with a flow of breathable gas;
a pressure communication conduit to connect the inlet chamber and the seal activation chamber for pressure communication such that a change in pressure in the inlet chamber changes the pressure in the seal activation chamber; and
a first flow control valve being coupled with the pressure communication conduit and being configured to selectively open and close the seal activation chamber to atmospheric pressure under control of the controller.

18. The apparatus of claim 17 wherein the flow generator comprises a motor, volute and an impeller configured between the gas inlet and the gas outlet.

19. The apparatus of claim 18 wherein the negative pressure in the seal activation chamber is discontinued when the first flow control valve is set to open the seal activation chamber to atmospheric pressure and wherein the discontinued negative pressure permits closure of the gas inlet to a flow of breathable gas.

20. The apparatus of claim 19 wherein the inlet flow seal comprises a flexible membrane.

21. The apparatus of claim 20 wherein the gas inlet comprises an aperture that is scalable by the inlet flow seal and wherein a surface area of the inlet flow seal is greater than an aperture area of the aperture.

22. The apparatus of claim 17 wherein, when the first flow control valve is set to permit equalization between the seal activation chamber and the gas inlet chamber, a back flow from the gas outlet to the gas inlet increases pressure in the inlet chamber and the seal activation chamber such that the increase in pressure permits closure of the gas inlet and whereby the back flow is stopped.

23. The apparatus of claim 17 further comprising a second flow control valve being coupled with the first flow control valve and being configured to selectively open and close the gas inlet to pressure of the gas outlet.

24. The apparatus of claim 23 wherein the first and the second control valves are configured to selectively seal a pressure level within the seal activation chamber such that the seal activation chamber discontinues equalizing with a pressure of the inlet chamber and an ambient pressure and wherein the sealed pressure level locks the inlet flow seal in an open position.

25. The apparatus of claim 24 wherein the second flow control valve is configured to selectively open and close a path to the first flow control valve to equalize with ambient pressure of the gas inlet and the first flow control valve is configured to selectively open and close the seal activation chamber to the second flow control valve.

26. The apparatus of claim 17 wherein the controller is further configured to set the first flow control valve in response to a detection of a condition of inspiration to permit a decrease in pressure in the seal activation chamber to open the gas inlet to a flow of breathable gas.

27. The apparatus of claim 26 wherein the controller is configured to set the first flow control valve in response to a detection of a condition of expiration to discontinue the decrease in pressure in the seal activation chamber to close the gas inlet to a flow of breathable gas.

28. The apparatus of claim 17 further comprising an oxygen input port coupled to the gas inlet to allow injection of oxygen gas into the gas inlet.

29. The apparatus of claim 17 further comprising an oxygen input port coupled to the gas outlet to allow injection of oxygen gas into the flow of breathable gas.

30. A system for regulating flow to a flow generator in a respiratory treatment apparatus, the system comprising:
a gas inlet to a flow generator through which a flow of breathable gas is adapted to be inspired;
means for sealing off the flow at the gas inlet, the means for sealing comprising a first side internally proximate to an inlet chamber of the gas inlet and a second side externally proximate to the inlet chamber of the gas inlet;
chamber means proximate to the second side of the means for sealing, wherein a negative pressure therein permits opening of the gas inlet at a location of the means for sealing;
means for changing pressure to the chamber means in accordance with a change in pressure in the gas inlet and for selectively discontinuing the change in pressure in the chamber means while permitting the change in pressure in the gas inlet; and
wherein a forward flow is prevented in accordance with an equalized pressure condition between the chamber means and ambient pressure.

31. The system of claim 30 further comprising an oxygen input port coupled to the gas inlet to allow injection of oxygen gas into the gas inlet.

32. The system of claim 30 further comprising an oxygen input port coupled to a gas outlet to allow injection of oxygen gas into the flow of breathable gas.

33. The system of claim 30 wherein a back flow is prevented in accordance with an equalized pressure condition between the chamber means and the gas inlet at the first side.

34. A system for regulating flow to a flow generator in a respiratory treatment apparatus, the system comprising:
a gas inlet to a flow generator through which a flow of breathable gas is adapted to be inspired;
means for sealing off the flow at the gas inlet, the means for sealing comprising a first side internally proximate to an inlet chamber of the gas inlet and a second side externally proximate to the inlet chamber of the gas inlet;
chamber means proximate to the second side of the means for sealing, wherein a negative pressure therein permits opening of the gas inlet with a flow of breathable gas;
means for changing pressure to the chamber means in accordance with a change in pressure in the gas inlet and for selectively discontinuing the change in pressure in the chamber means while permitting the change in pressure in the gas inlet; and
means for sealing pressure in the chamber means;
wherein a back flow is permitted in accordance with a sealed pressure condition of the chamber means that locks open the means for sealing off the flow.

35. The system of claim 34 further comprising an oxygen input port coupled to the gas inlet to allow injection of oxygen gas into the gas inlet.

36. The system of claim 34 further comprising an oxygen input port coupled to a gas outlet to allow injection of oxygen gas into the flow of breathable gas.

37. The system of claim 34 wherein a back flow is prevented in accordance with an equalized pressure condition between the chamber means and the gas inlet at the first side.

* * * * *